United States Patent [19]

Hibino et al.

[11] Patent Number: 4,866,516
[45] Date of Patent: Sep. 12, 1989

[54] OPTICAL ENDOSCOPE HAVING IMAGE SIGNAL TRANSMITTING CABLE

[75] Inventors: Hiroki Hibino, Hachioji; Kenji Kimura, Tachikawa, both of Japan

[73] Assignee: Olympus Optical Co., Ltd., Tokyo, Japan

[21] Appl. No.: 205,253

[22] Filed: Jun. 10, 1988

[30] Foreign Application Priority Data

Jun. 12, 1987 [JP] Japan .................. 62-146769
Jan. 8, 1988 [JP] Japan .................... 63-2043
Apr. 1, 1988 [JP] Japan ................... 63-81800

[51] Int. Cl.$^4$ ............................ A61B 1/04; A61B 1/06
[52] U.S. Cl. .................................. 358/98; 128/6
[58] Field of Search .............................. 358/98; 128/6

[56] References Cited

U.S. PATENT DOCUMENTS

| | | | |
|---|---|---|---|
| 4,413,278 | 11/1983 | Feinbloom | 358/98 |
| 4,475,539 | 10/1984 | Konomura | 128/6 |
| 4,590,923 | 5/1986 | Watanabe | 128/6 |
| 4,601,284 | 7/1986 | Arakawa | 128/6 |
| 4,621,618 | 11/1986 | Omagari | 128/6 |
| 4,646,724 | 3/1987 | Sato | 128/6 |
| 4,722,000 | 1/1988 | Chatenever | 358/98 |
| 4,797,737 | 1/1989 | Yazawa | 358/98 |

FOREIGN PATENT DOCUMENTS 59-69054 4/1984 Japan .
60-243625 12/1985 Japan .

Primary Examiner—Howard W. Britton
Attorney, Agent, or Firm—Armstrong, Nikaido, Marmelstein, Kubovcik & Murray

[57] ABSTRACT

An endoscope system having an elongated insertion portion, an endoscope provided with an image guide disposed in the elongated insertion portion and adapted to transmit an optical image, and an ocular portion facing an emergence-end surface of the image guide. A transmission line for transmitting an image signal supplied from an imaging unit having an imaging means and capable of being mounted on the ocular portion is provided on the side of the endoscope, thereby eliminating the need for leading any cable out of the imaging unit.

54 Claims, 19 Drawing Sheets

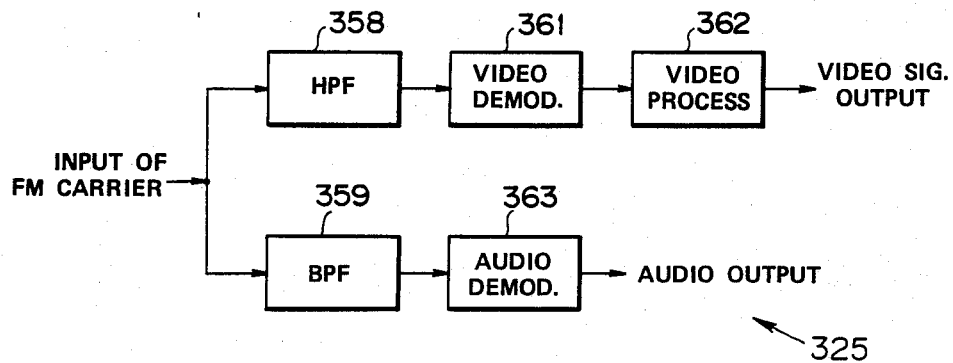
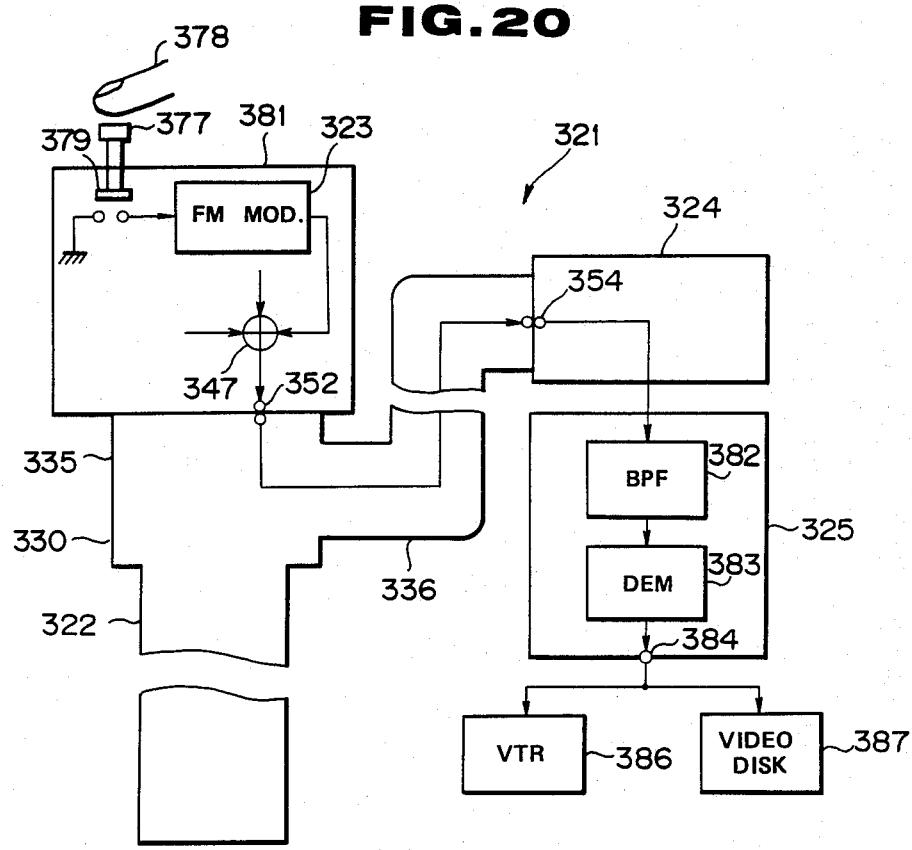

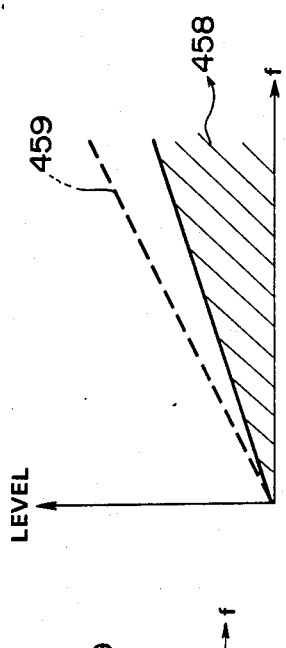
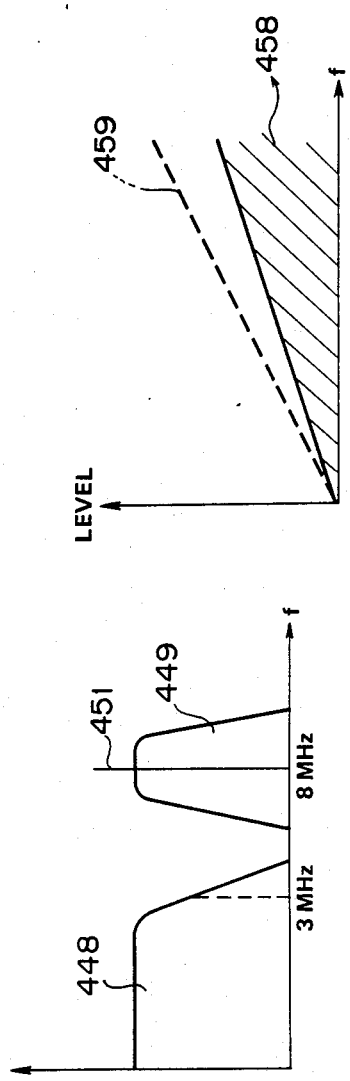
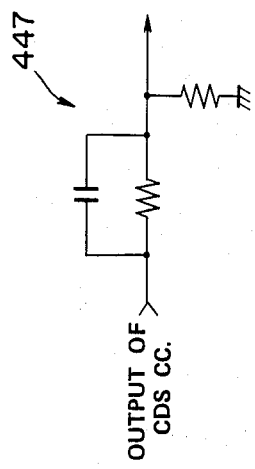

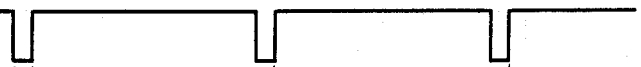
FIG. 25a HOR. SYNC. SIG.
FIG. 25b CHARGE TRANSF. SIG.
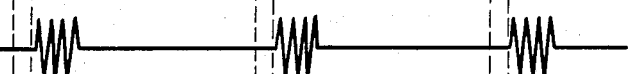
FIG. 25c BURST SIG.
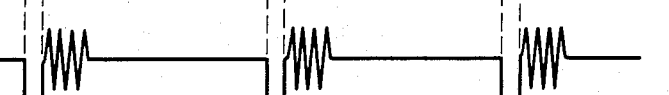
FIG. 25d OUTPUT OF SIG. GEN.
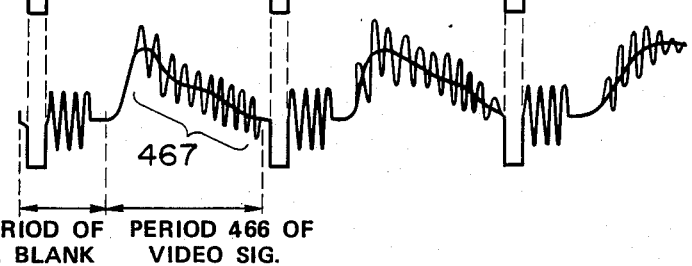
FIG. 25e OUTPUT OF MIXER
PERIOD OF H. BLANK     PERIOD 466 OF VIDEO SIG.
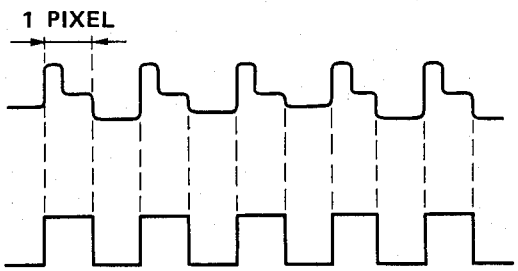
FIG. 26a WAVE FORM OF CCD OUT
FIG. 26b CHARGE TR. SIG.

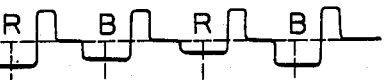
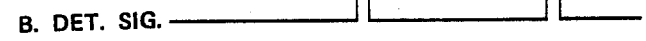
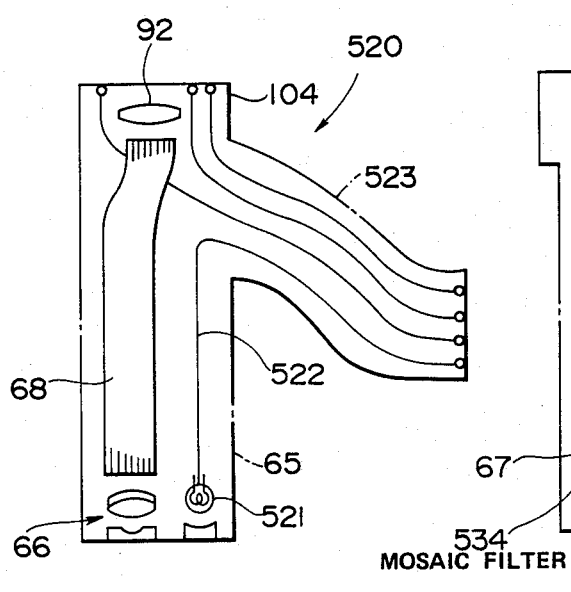
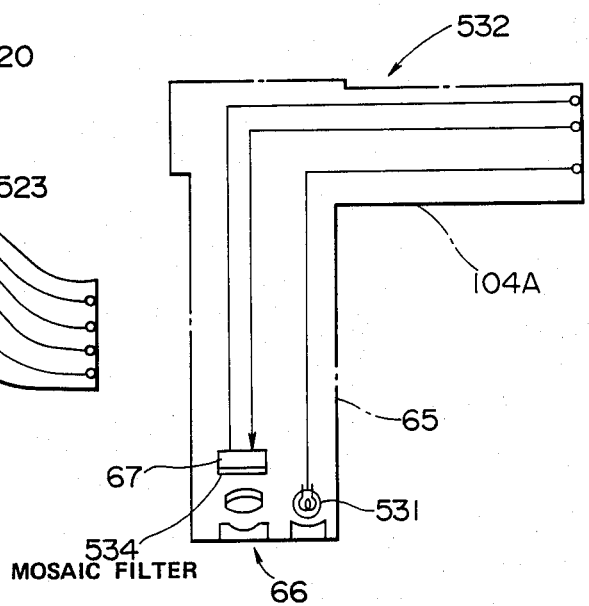

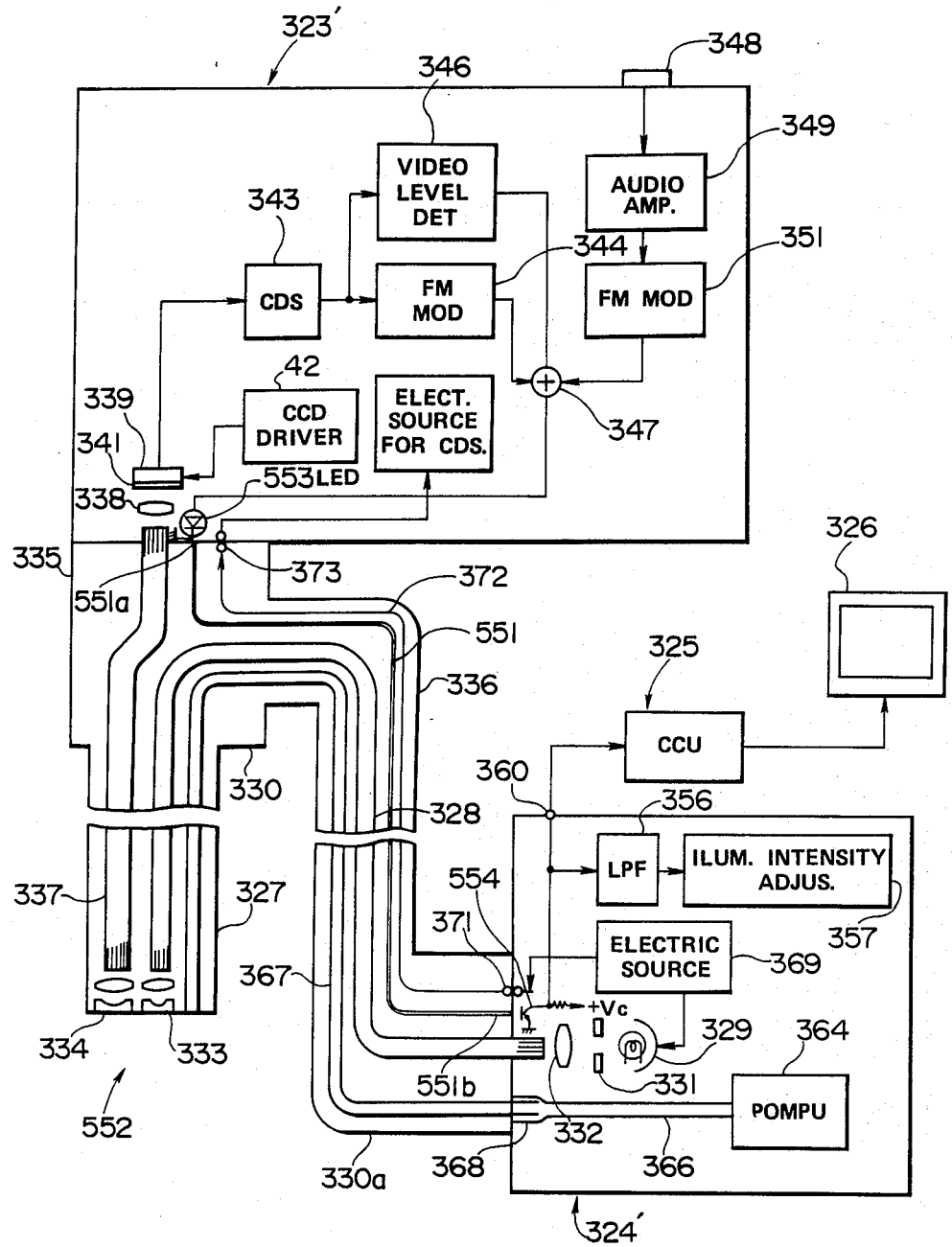

OPTICAL ENDOSCOPE HAVING IMAGE SIGNAL TRANSMITTING CABLE

BACKGROUND OF THE INVENTION

Industrial Field of the Invention and Related Art

This invention relates to an optical endoscope having an ocular portion and provided with an image signal transmission cable.

Endoscopes have in recent years been widely used to enable the affected parts of a body to be observed without the necessity for cutting the same in the body cavity, and, if necessary, treatment can be conducted with the use of tools suitable for the treatment required.

An electronic type of endoscope (abbreviated as "electronic endoscope" hereinafter) which employs a solid imaging device as an imaging means has in recent years been put into practical use. In such endoscopes, the endoscope image can be easily displayed on a monitor and recording and reproduction of the image can also be conducted easily.

In an optical endoscope using an image guide (also can be called "fiber scope"), recording and reproduction of the endoscope image can be conducted with the use of an external TV camera.

A conventional type of endoscope on which an external TV camera is mounted is shown in FIG. 1.

Referring to FIG. 1, in a fiber scope 601, image of an object is transmitted to a handling portion 603 of an endoscope through an image guide 602, and illuminating light is transmitted to the object through a light guide 606 which passes through a light guide cable 605 connected to a light source device 604. An optical image obtained through the image guide 602 is imaged on an imaging surface of a charge coupled device which functions as a solid imaging device (abbreviated as "CCD" hereinafter) 609 by means of an optical imaging system in an external TV camera 608 connected to an ocular portion 607 of the fiber scope 601. The optical image imaged on the CCD 609 is photoelectrically converted, and is input to a signal processing circuit 611 where it is signal-processed and output as an image signal. This image signal is transmitted to a camera control unit 613 through a plurality of transmission cables 612 that pass through a signal cable 610. A plurality of power cables (omitted from the illustration) through which power can be supplied from the camera control unit 613 to the external TV camera 608 are further passed through this signal cable 610.

The above-described camera control unit 613 converts the image signal into, for example, an NTSC combined image signal, and which is input to a TV monitor 614 so that the image of the object may be displayed on the screen of the TV monitor 614.

As shown in FIG. 1, in the conventional example, the signal cable 610 through which the transmission cable 612 for transmitting an image signal is passed connects the external TV camera 608 and the camera control unit 613. The light guide 606 and a light guide cable 605 through which an air flowing pipe or a forceps (omitted from the illustration) are passed connects the endoscope handling portion 603 and the light source device 604.

In the conventional example, since the cables 605 and 610 are respectively extended from the fiber scope 601 and the TV camera 608 which are capable of being separated from each other, these cables can easily get caught during usage. Therefore, if the fiber scope 601 is intended to be used solely with the TV camera 608 removed, it is sometimes difficult to completely separate them from each other.

Furthermore, in a case where the TV camera 608 is connected, since the two cables 605 and 610 are extended from two different places, they will inevitably tend to interfere with handling.

OBJECT AND SUMMARY OF THE INVENTION

An object of the present invention is to provide an optical endoscope having an image signal transmitting cable which is easy to handle.

Another object of the present invention is to provide an optical endoscope having an image signal transmitting cable which can be used in a manner similar to that in which the electronic endoscope is used.

A still further object of the present invention is to provide an endoscope which allows an imaging unit to be easily attached thereto and detached therefrom. In the present invention, an optical endoscope is provided in which an insertion portion thereof is provided with means allowing illuminating light to emerge, an object optical system, and an image guide, and an ocular portion thereof which confronts the light emerging end of the image guide is able to be connected to an imaging unit including an imaging means, the optical endoscope being characterized in that a signal cable for transmitting an image signal is passed through a cable whose one end is positioned in the ocular portion, and which outwardly extends from the rear end of the insertion portion or the ocular portion. Consequently the endoscope can be used in a manner similar to that of an electronic endoscope simply by connecting an imaging unit.

BRIEF DESCRIPTION OF THE DRAWINGS

FIGS. 2 to 4 illustrate a first embodiment of the present invention, wherein

FIG. 2 illustrates the structure of a state in which a fiber scope to which an external TV camera is connected is connected to a signal processing portion;

FIG. 3 illustrates the structure of a state in which an electronic scope is connected to the signal processing portion;

FIG. 4 is a schematic perspective view of the whole body of the system according to a first embodiment;

FIGS. 16 to 19 illustrate a seventh embodiment of the present invention, wherein FIG. 16 illustrates the structure of an endoscope;

FIG. 17 illustrates the band range of an image signal output by a CDS circuit;

FIG. 18 illustrates the band range of an output signal from an FM modulator;

FIG. 19 is a block diagram illustrating the structure of a signal processing system of a camera control unit;

FIG. 20 illustrates an essential portion of a eighth embodiment of the present invention;

FIGS. 21 to 28 illustrate a ninth embodiment of the present invention, wherein

FIG. 21 illustrates the structure of an endoscope according to the ninth embodiment;

FIG. 22 illustrates the band range of an output signal from a CDS circuit;

FIG. 23 illustrates the fact that the levels of the signal and noise at the transmitting cable depend upon the frequency;

FIG. 24 is a circuit diagram illustrating a specific example of a high band emphasizing circuit;

FIGS. 25a-25e illustrate the operation of the ninth embodiment;

FIGS. 26a and 26b illustrate the waveforms of signals read from CCD by a CCD driving circuit;

FIG. 27 illustrates the structure of a PLL;

FIGS. 28a-28c illustrate the state in which R and B-signals are detected with respect to a CCD output signal;

FIG. 30 is a schematic view illustrating the structure of a fiber scope to which a lamp is connected;

FIG. 31 is a schematic view illustrating the structure of an electronic scope to which a lamp is connected; and FIG. 32 illustrates the structure of an endoscope according to a eleventh embodiment of the present invention.

DETAILED DESCRIPTION OF THE PREFERRED EMBODIMENT

Figure 4:
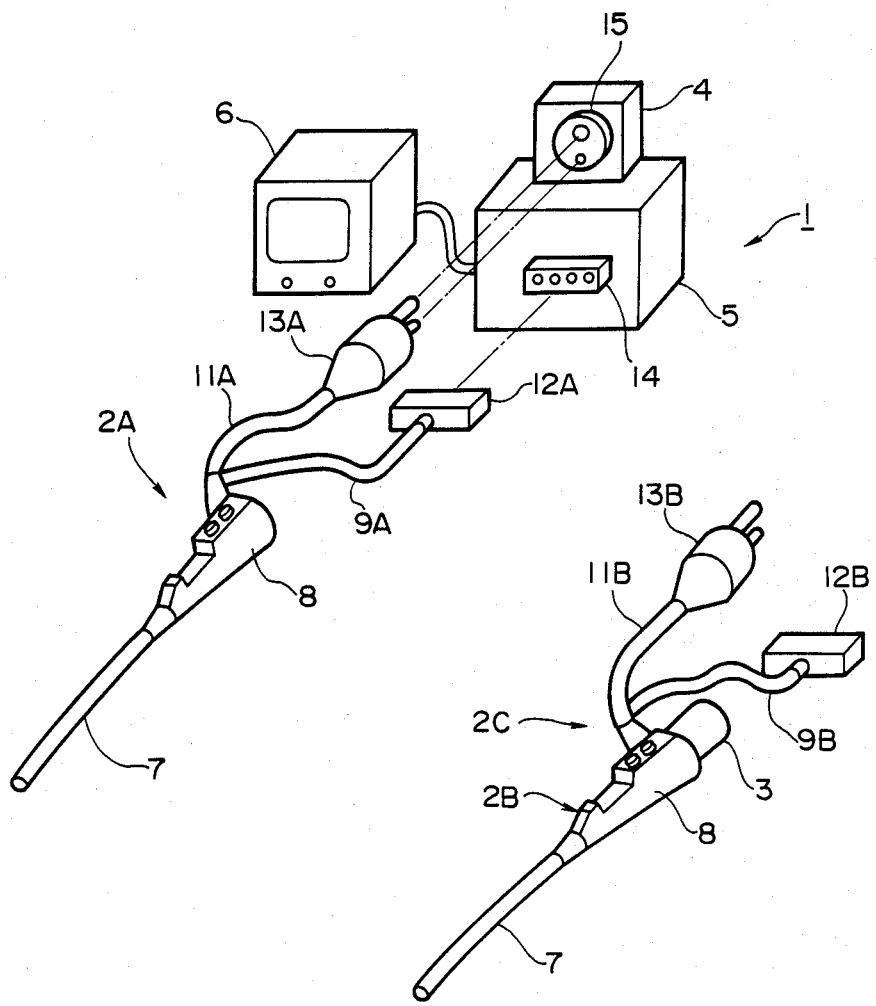

As shown in FIG. 4, an endoscope imaging device 1 according to a first embodiment comprises an electronic endoscope 2A (abbreviated as "electronic scope" hereinafter) including a photographing means; a device 2C (abbreviated as "external camera equipped scope" hereinafter) constituted by a fiber scope 2B and a TV camera 3 which can be fitted from outside, and which is connected to the fiber scope 2B; a light source device 4 for supplying illuminating light to the scopes 2A, 2B, and 2C (represented by 2 hereinafter); a signal processing portion 5 provided with a TV signal processing circuit means to which output signals from the two scopes 2A and 2C are input, and which outputs the signals after converting them into TV signals; and a monitor 6 for displaying the TV signals output from the signal processing portion 5 in the from of an image.

Each of the above-described scopes 2 has an elongated insertion portion 7 which is provided with a handling portion 8 of a large width at the rear end of the insertion portion 7. The above-described electronic scope 2A and fiber scope 2B have the corresponding handling portion 8 from which two universal cables 9A, 11A or 9B, 11B are branched. Signal connectors 12A and 12B are respectively connected to the corresponding signal-transmissible universal cables 9A and 9B, while light source connectors 13A and 13B are respectively connected to the corresponding light source universal cables 11A and 11B.

The above-described signal connectors 12A and 12B can be connected to a connector receiver 14 disposed on the front surface of the signal processing portion 5, while the light source connectors 13A and 13B can be connected to a light source connector receiver 15 of the light source device 4.

Figure 3:
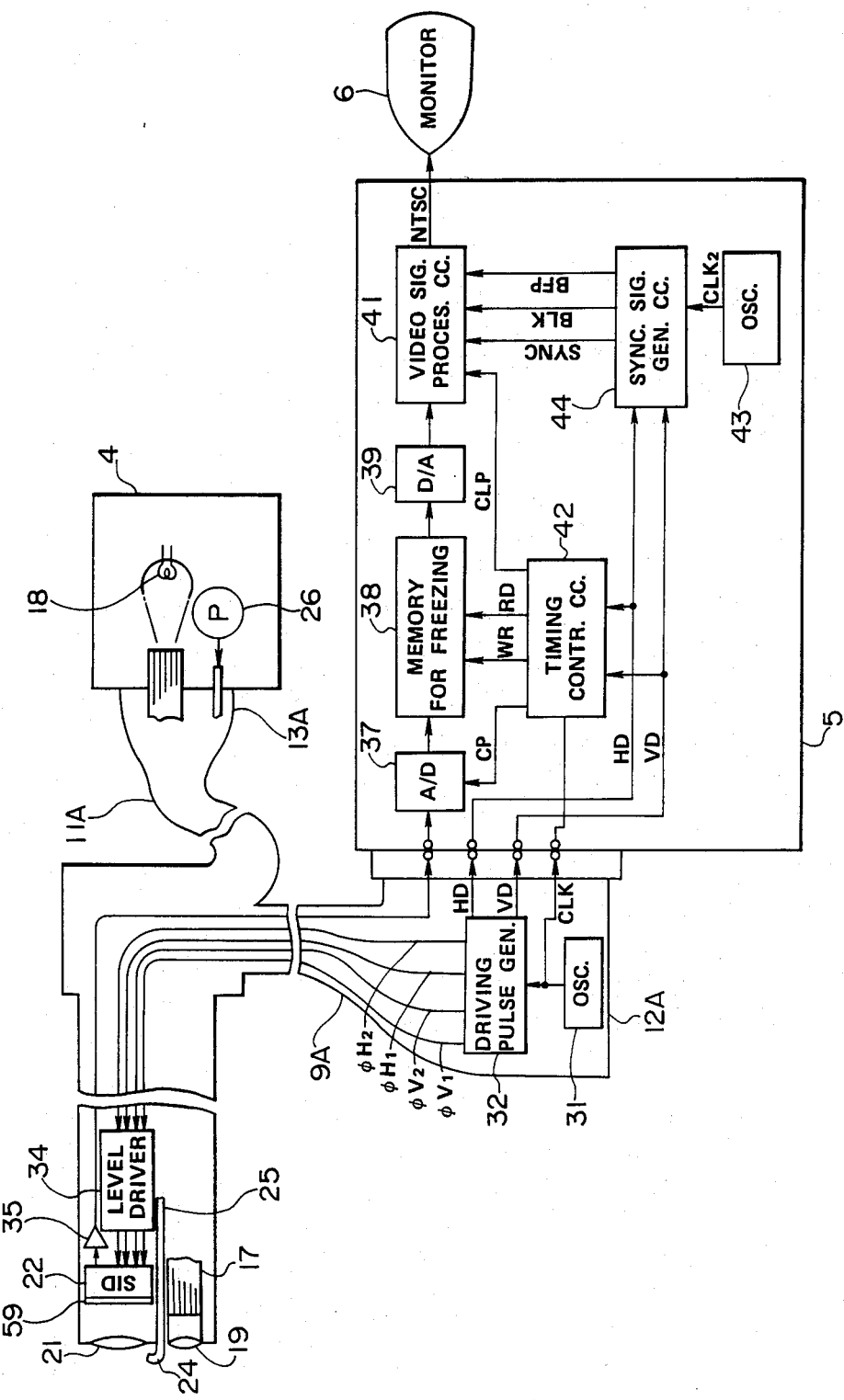

The electronic scope 2A and the fiber scope 2B each has the insertion portion 7 through which a light guide 17 passes, the light guide 17 being further passes through the other universal cables 11A and 11B. By connecting the light guide 17 with the light source device 4 as shown in FIG. 3 or FIG. 4, the illuminating light emerged from the light source lamp 18 is supplied so that it is issued from the front end surface of the insertion portion 7 with the aid of a light distribution lens 19 to the object in the light diffused form. The insertion portion 7 is provided with an object lens 21 at the front end thereof in such a manner that, in the case of the electronic scope 2A, the imaging surface of a solid imaging device 22 (abbreviated as "SID" hereinafter) confronts the focusing surface thereof, while in the case of the fiber scope 2B, the front end surface of an image guide 23 confronts the same. A nozzle is provided adjacent to the object lens 21 for the purpose of washing the object lens 21, the nozzle 24 being able to be connected to the air/water supplying pump 26 disposed in the light source device 4 via an air/water supplying conduit run 25.

The electronic scope 2A, as shown in FIG. 3, comprises the connector 12A which accommodates an oscillator 31 and a driving pulse generator circuit 32. As a result of this, the driving pulse generating circuit 32, in accordance with reference clock CLK of the generator 31, generates (for example, two-phase) SD driving signals (that is, horizontal driving pulses) $\phi H1$ and $\phi H2$, vertical driving pulses $\phi V1$ and $\phi V2$, and horizontal synchronizing signal HD and vertical synchronizing signal VD.

These driving signals $\phi H1$, $\phi H2$, $\phi V1$, and $\phi V2$ are supplied to an SID 22 via a level driver 34 disposed adjacent to the SID 22.

The signal of the image obtained by the SID 22 can be output by way of supplying the driving signal to the SID 22 after properly amplifying the level of the driving signal. This signal is amplified by an amplifier 35 disposed adjacent to the SID 22, and is input to the signal processing portion 5 via a signal cable.

The signal input to the signal processing portion 5 is converted into a digital signal by an A/D converter 37, and is written in a freezing memory 38. The signal data written in the freezing memory 38 is converted into an analog signal by a D/A converter 39, and is input to an image signal processing circuit 41. As a result of this, it is converted into an NTSC type of color image signal by this image signal processing circuit 41, and is displayed by the monitor 6.

The horizontal and vertical driving pulses $\phi H1$, $\phi H2$ of the driving pulse generating circuit 32 and the clock CLK of the oscillator 31 are input to a timing control circuit 42, whereby clock CP which is converted in an analog-digital manner is supplied to the A/D converter 37, a read/write control signal RD/WR is supplied to the freezing memory 38, and a clamp signal CLP is supplied to the image signal processing circuit 41.

The above-described horizontal and vertical synchronizing signals HD and VD and reference clock CLK2 of a second oscillator 43 are input to a synchronizing signal generating circuit 44. This synchronizing signal generating circuit 44 generates combined synchronizing signal SYNC, blanking signal BLK, and burst pulse BFP, and inputs them to the image signal generating circuit 41 so as to generate a predetermined NTSC type of image signal.

Figure 2:
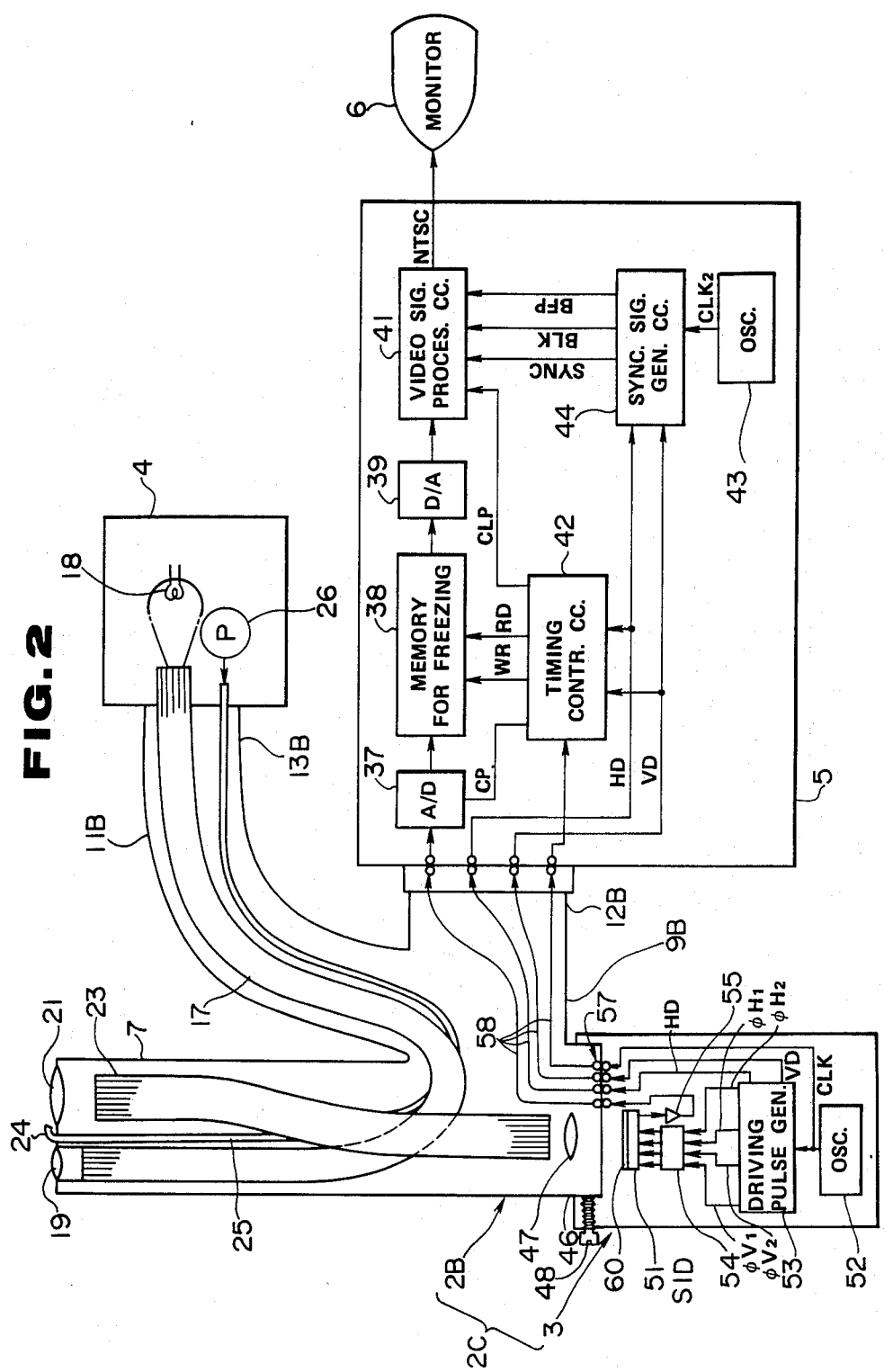

The fiber scope 2B, as shown in FIG. 2, transmits an optical image to its rear end surface through the image guide 23. As a result of this, the image can be observed in an enlarged manner with naked eyes through an ocular lens 47 disposed in an ocular portion 46.

The ocular portion 46 is adapted to detachably connect the external mounting TV camera 3 having a screw 48 as mounting means (See FIG. 2). This external TV camera 3 includes an SID 51 facing to said ocular lens 47, an oscillator 52 for generating reference clock CLK, a driving pulse generating circuit 53 for generating, in response to the clock CLK, the driving signals $\phi$H1, $\phi$H2, $\phi$V1, and $\phi$V2, and as well generating horizontal and vertical synchronizing signals HD and VD, a level driver 54 which amplifies these driving signals and supplying them to the SID 51, and an amplifier 55 for amplifying the signal read out from the SID 51 in response to the driving signal applied to the SID 22 via the level driver 54.

The signal which has been amplified by the amplifier 55, the clock CLK of the oscillator 52, and the horizontal and vertical synchronizing signals HD and VD are connected to contacts disposed on the side confronting the ocular portion 46. As a result of this, when the external TV camera 3 is connected to the ocular portion 46 of the fiber scope 2B, the contacts are arranged to be connected to connecting contacts 57 provided for the ocular portion 46. The signals supplied to the contacts 57 are transmitted to a connector 12B via a cable 58 which is passed through the universal cable 12B of the fiber scope 2B. By connecting this connector 12B with a connector receiver 14 of the signal processing portion 5, the signal processing similar to that conducted in the case of the electronic scope 2A can be conducted. The imaging surfaces of the SIDs 22 and 51 which are respectively included in the electronic scope 2A and the external TV camera 3 are provided with mosaic filters 59 and 60 respectively so that each picture element is color-divided into red, green and blue, and color imaging can be conducted under white illumination.

The reason for the fact that the electronic scope 2A and the external camera 3 are respectively provided with the generator 31 or 52 and the driving pulse generating circuit 32 or 53 lies in that the imaging can be conducted with the clock signal CLK corresponding to the number of the picture elements even if the number of the devices is different between that of the SID 22 and that of SID 51. As the number of the picture elements becomes greater, the clock signal CLK set also becomes high level. Meanwhile, if each clock signal CLK varies, the dividing pulse generating circuits 32 and 53 output the synchronizing signals HD and VD with the same frequency, whereby a predetermined image signal is generated, as a result of which, the image can be displayed with a usual monitor.

According to the first embodiment whose structure has been described above, when, for example, the electronic scope 2A is used, the endoscope image obtained by the electronic scope 2A can be observed on the monitor 6 by connecting the two connectors 12A and 13A of the electronic scope 2A to the corresponding connector receivers 14 and 15 of the signal processing portion 5 and the light source device 4. When the scope 2C to which the TV camera 3 is connected is used as the fiber scope 2B, it is only necessary to connect the TV camera 3, and the connectors can be used in the similar manner to that in the case of the electronic scope 2A. In this case, since any cable is not extended from the TV camera 3, the TV camera can be easily attached and detached. Therefore, a problem experienced in the prior art can be overcome, the problem being arisen in that the cable extended from the camera is easily caught by the cable of the fiber scope, and they are difficult to be separated from each other.

Furthermore, since the conditions of the cables extended outside are similar to the case of the electronic scope 2A and the case of the external camera equipped scope 2C, the way to draw the cable in the direction in which any catch of cables does not occur which is employed in the case of using the electronic scope 2A can be as it is employed also in the case of the external camera equipped scope 2C (it is not necessary for respective scopes to employ different ways), as a result of which, handling can be improved.

It is apparent that the first embodiment can be applied to the fiber scope 2B. In the case of the fiber scope 2B, the signal processing portion 5 is not needed to be provided, but it can be used with the connection maintained.

Although in the first embodiment, the light source device 4 and the signal processing portion 5 are individually provided, they may be coupled so as to form a video processor. In this case, the universal cables 9A and 11A or 9B and 11B may be, as it is, two cables or may be combined into a single cable.

Although the power source line is omitted from the illustration, it may be arranged from the signal processing portion to the TV camera with a universal cable.

Figure 5:
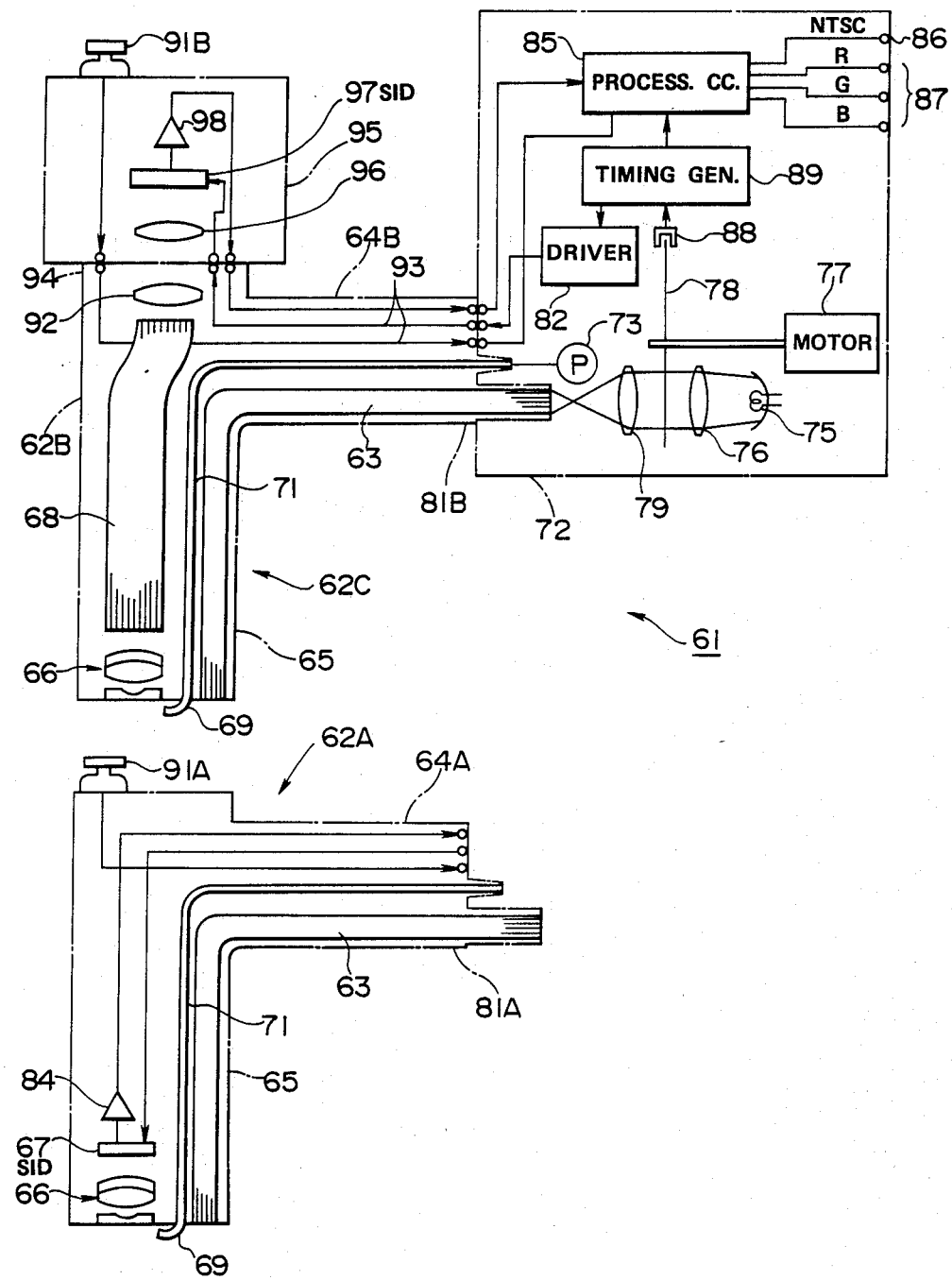
FIG. 5 illustrates the structure of a second embodiment according to the present invention.

FIG. 5 illustrates a second embodiment of the present invention in which a plane sequential imaging is conducted in comparison to the first embodiment which comprises an imaging means in which color filters are included for conducting the color imaging under a white illumination, a light source for illuminating the imaging means, and a signal processing system (expressed as a "synchronous system").

A light guide 63 is, similarly to the first embodiment, passed through an electronic scope 62A and a scope 62C which is so constituted that an external camera 95 is connected to a fiber scope 62B, which form an imaging device 61 according to the second embodiment. This light guide 63 is also passed through universal cables 64A and 64B, respectively. Similarly, at each of the front end portions of the insertion portions 65 of the two scopes 62A and 62B (or 62C) is provided with an object lens 66. It is so constituted that the imaging surface of an SID 67 and the front end surface of an image guide 68 confront the focusing surface of the object lens 66.

The two scopes 62A and 62B are each provided with a nozzle 69 in such a manner that the nozzle 69 confronts the outer surface of the above-described object lens 66, the nozzle 69 being connected to an air/water supplying conduit run 71 so that air or water can be supplied from an air/water supplying pump 73 after they have been connected to the connector receiver of a video processor 72.

The above-described video processor 72 accommodates a plane sequential type of light source means and a plane sequential type of signal processing means.

That is, the white light emerged from the light source lamp 75 is formed into a parallel light beam by a collimeter lens 76, and is applied to the rotatable filter 78 rotated by a motor 77.

Figure 1:
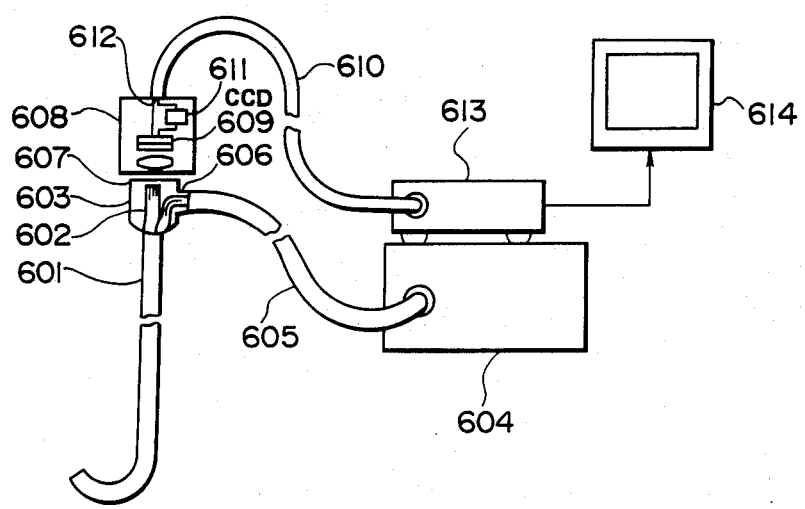
FIG. 1 illustrates the structure of a related art.
Figure 6:
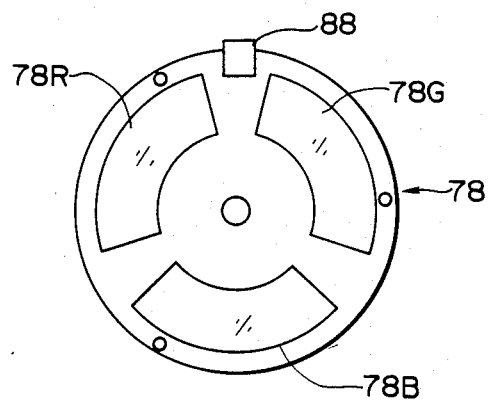
FIG. 6 is a front view of a rotatable filter according to the second embodiment.

The rotatable filter 78 is, as shown in FIG. 6, provided with color transmissible filters 78R, 78G, and 78B, which respectively transmits red, green, and blue light beam, at the corresponding three fanwise openings disposed in sequence in the circumferential direction of a disc-shaped light shield plate. As a result of this, when the rotatable filter 78 is rotated, the color transmissible filters 78R, 78G, and 78B each of which corresponding to red, green, and blue are sequentially interrupt the light passage. As a result of this, the light which has been passed through the rotatable filter 78 is made a plane sequential light of red, green, and blue. The plane sequential light is converged by a condenser lens 79 and is applied to the light-incidental end surface of the light guide 63.

The object illuminated by the illuminating light which comprises the sequential light is imaged on the SID 67 in the case of the electronic scope 62A. Therefore, the driving signal of a driver 82 is supplied to the SID 67 via an electrical contact after a connector 81A has been connected to the connector receiver of the video processor 72 so that the electric signal representing the image obtained by the SID 67 is output. This signal is then amplified by an amplifier 84, and is input to a plane sequential type of processing circuit 85 whereby it is converted into an NTSC type of combined image signal and signals each representing red, green, and blue. The thus-converted signals are output to the monitor (omitted from the illustration) through the output terminals 86 and 87.

The rotatable filter 78 is provided with a sensor 88 which detects the rotational position, the sensor 88 detecting when each irradiation with red, green, and blue is completed. The thus generated detection signal is input to a timing generator 89 which causes a driver 82 to output driving signals for reading signals when the illuminating period is completed. This timing generator 89 also supplies timing signals to the process circuit 85 so that control of the writing to a plurality of memories is conducted by switching.

The electronic scope 62A and the external TV camera 95 are provided with freezing switches 91A and 91B. The freezing switches 91A and 91B are adapted to control the writing to frame memories (omitted from the illustration) disposed in the process circuit 85 via a signal cable. That is, when the freezing switches 91A and 91B are switched on, writing to the frame memories are stopped, and the image data prior to the switch switching on is maintained. As a result of this, a frozen image (still image) is displayed on the monitor (omitted from the illustration). On the other hand, when the same is switched off, or when the same is again pressed, the freezing is released, as a result of which, normal kinetic image is displayed.

In the case of the external camera equipped scope 62C, an optical image transmitted through the image guide 68 is imaged on an SID 97 by means of an ocular lens 92 and an imaging lens 96 included in the external TV camera 95 attached to an ocular portion 94 of the fiber scope 62B. A driving signal output from the driver 82 is, similarly to the case of the electronic scope 62A, supplied to the SID 97. The signal which has been read from the SID 97 is amplified by a preamplifier 98, and is input to the process circuit 85.

In this case, the electrical contact disposed on the external TV camera 95 is connected with the contact of the fiber scope 62B so that the electrical signals can be transmitted between the SID 97 and the video processor 72 through a signal cable 93 included by the fiber scope 62B.

The second embodiment is mainly characterized in that the color filter included type of imaging device according to the first embodiment is changed to a plane sequential type and that the universal cables are combined into a single cable. Furthermore, a freezing operation can be conducted.

The operation and effect of the second embodiment are similar to those obtained in the first embodiment, but since a single universal cable is employed, it does not interfere the handling, and the system is easier to be handled.

Figure 7:
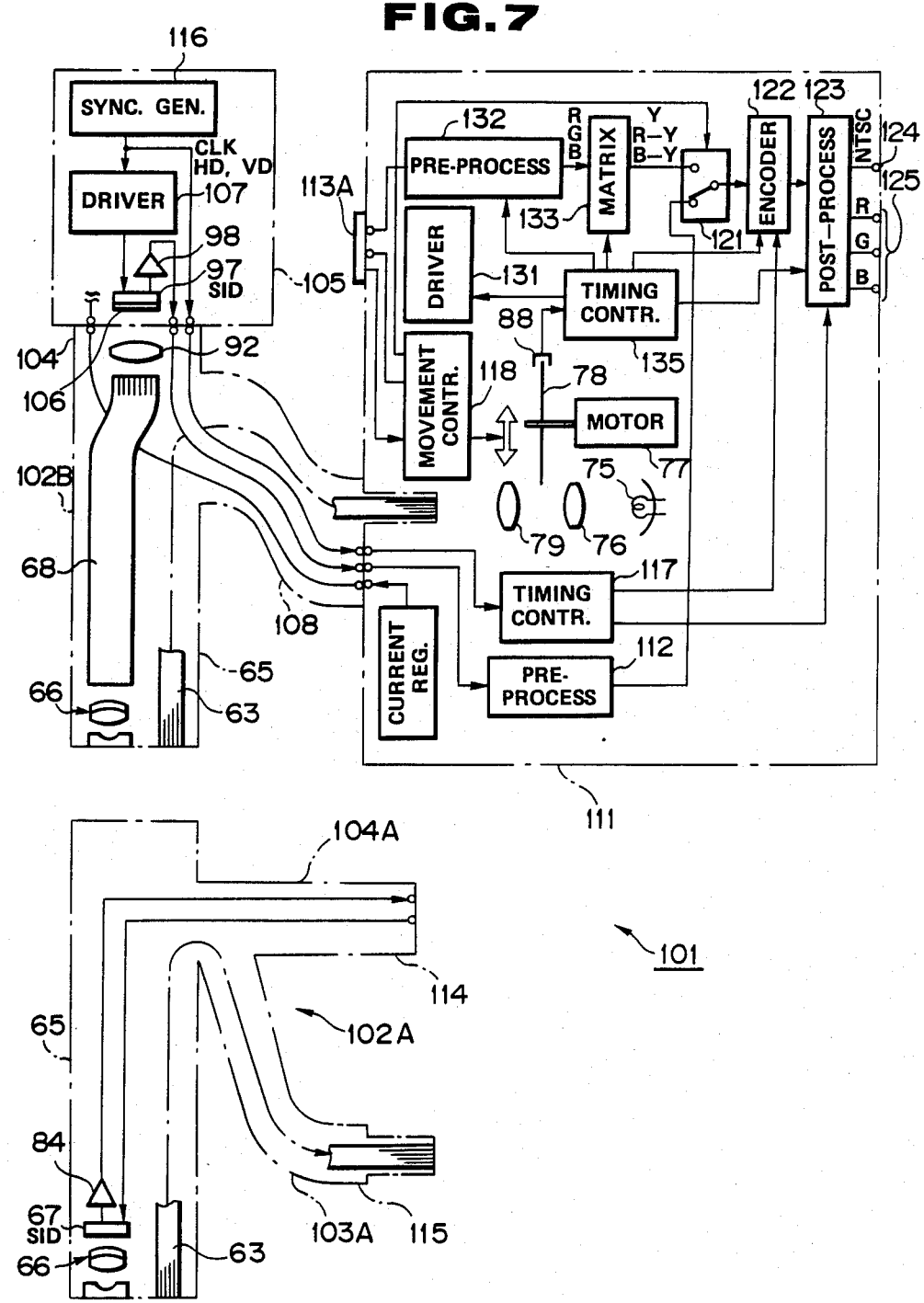
FIG. 7 illustrates the structure of a third embodiment of the present invention.

FIG. 7 illustrates a third embodiment.

An imaging device 101 according to the third embodiment is characterized in that a plane sequential type of electronic scope 102A is employed and that it can be used even if the TV camera 105 is a synchronous type.

The electronic scope 102A differs from the electronic scope 62A shown in FIG. 5 in that the release switch 91A is not provided (therefore, the signal cable which transmits its signal is not also provided), and that the single universal cable 64A is branched into two cables; a light guide cable 103A and a universal cable 104A. The same parts as those illustrated in FIG. 5 are given the same reference numerals.

A TV camera 105 connected to an ocular portion 104 of the fiber scope 102B is so constituted that the TV camera 95 shown in FIG. 5 has the SID 97 whose front surface is provided with a mosaic filter 106. A driving signal is supplied from a driver 107 disposed in the TV camera 105 to the SID 97. The signal which has been read out is arranged to be input to a preprocess circuit 112 of a video processor 111 via a signal cable which has been passed together with the light guide 63 through a single universal cable 108 after it has been passed through the preamplifier 98. In this case, the video processor 111 is provided with a light guide connector receiver and a synchronous signal connector receiver which are disposed adjacently each other. The video processor 111 is further provided with a plane sequential signal connector receiver 113A at the other position of the former two types of connector receivers. The connector receiver 113A is arranged to connect a signal connector 114 disposed at the end portion of the universal cable 104A in the electronic scope 102A. The light guide connector 115 of the electronic scope 102A is arranged to be connected to common connector receivers.

The TV camera 105 accommodates a synchronous generator 116 so that clock signal CLK, horizontal and vertical synchronizing signals HD and VD are supplied to the driver 107, and the same are also supplied to a timing control circuit 117 in the video processor 111 via the signal cable in the universal cable 108 in the fiber scope 102B.

The light source means in the video processor 111 supplies white light to the light guide 63 when the signal connector 114 of the electronic scope 102A is not connected as shown in FIG. 7.

The light source means is so constituted that the motor 77 and the rotatable filter 78 rotated by the motor 77 provided for the light source means shown in FIG. 5 are movably provided by a movement control mechanism 118. The rotatable filter 78 usually, as shown in FIG. 7, is withdrawn (for example moved upwardly) from the light passage, causing white lighting to be performed. However, when the signal connector 114 of the electronic scope 102A is connected, the fact that the connection is realized is detected by the movement control mechanism 118, and the rotatable filter 78 shown in FIG. 7 is moved downwardly together with the motor 77, as a result of which, the rotatable filter 78 is interposed in the light passage in order to perform the plane sequential lighting.

Figure 8:
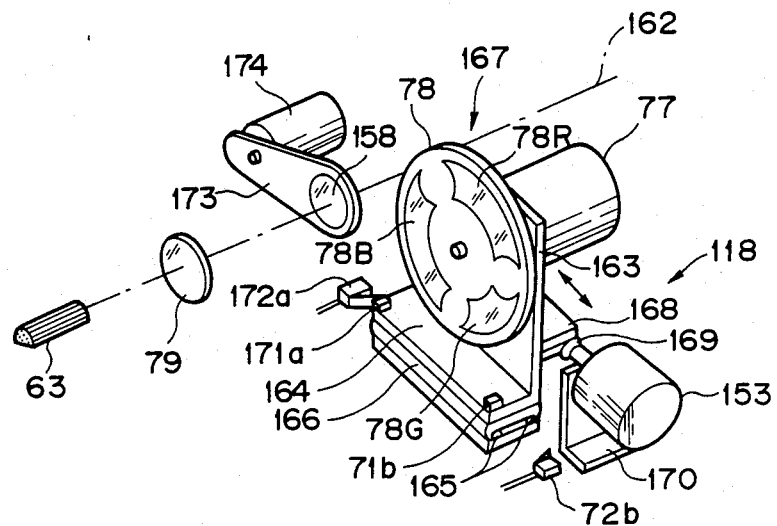
FIG. 8 is a perspective view of a rotatable filter moving mechanism according to the third embodiment.

The above-described light source means is shown in FIG. 8.

The above-described rotatable filter 78 and the motor 77 which rotates the former are moved by the movement control mechanism 118 shown in FIG. 8 and are able to withdraw from the optical axis 162. That is, the motor 77 is fixed to a plate-like fitting bracket 163 having a flange portion 164 at the lower portion thereof, the flange portion 164 being horizontally bent. Two rails 165 and 165 are in parallel provided beneath the flange portion 164, the two rails 165 and 165 being fixed to the housing of the video processor 111. The flange portion 164 is provided with at the bottom thereof a slide portion 166 which is so formed that it holds the two parallel rails 165 and 165 from the two sides. The slide portion 166 is arranged to slidably hold the two rails 165 and 165, as a result of which, the a rotatable filter portion 167 comprising the rotatable filter 78, motor 77 and the position sensor 88 can be moved.

The fitting bracket 163 is provided with a rack gear 168 along the direction of movement of the rotatable filter portion 167 on the side thereof which is to be fitted to the light source lamp (omitted from the illustration). A worm gear 169 which is rotated by a motor 153 for moving is engaged with the rack gear 168. The motor 153 is fixed to the housing of the video processor 111 with a bracket 170. When the motor 153 is rotated forward or reversely, the above-described filter portion 167 can be moved with the aid of the above-described worm gear 169 and the rack gear 168.

The upper surface of the flange portion 166 of the above-described fitting bracket 163 is provided with, at its two ends in the direction of movement, projecting flat portions 171a and 171b in the form of a prism, the flat portions 171a and 171b being adapted to press switches. At the two ends of the movable range of the above-described rotatable filter portion 167, microswitches 172a and 172b for detecting the position at which the switching is conducted are respectively provided at the positions corresponding to the above-described portions 171a and 171b for pressing the microswitches 172a and 172b. When the microswitches 172a and 172b are pressed by the portions 171a and 171b, the fact is detected that the above-described rotatable filter portion 167 reaches its movable limit, and the rotation of the above-described motor 153 is stopped, causing the movable region through which the rotatable filter portion 167 can be moved to be limited.

In the embodiment as illustrated, when the portion 171a presses the microswitch 172a, the color transmissible filters 78R, 78G, and 78B of the rotatable filter 78 is interposed on the above-described optical axis 162 so that white light is allowed to pass through the above-described color transmissible filters 78R, 78G, and 78B. On the other hand, when the portion 171b presses the microswitch 172b, the above-described rotatable filter 78 is arranged to withdraw from the above-described optical axis 162. In this state, a solenoid 174 for realizing a rotational motion whose rotational shaft journals a rotational arm 173 to which a concave lens 158 is fitted is arranged to work in synchronization with the movement of the above-described rotatable filter 78, the solenoid 174 being omitted from detail description in its structure. The concave lens 158 fitted at the front end of the rotatable arm 173 of the solenoid 174 for realizing a rotational motion is arranged to be rotated and interposed on optical axis 162.

As a result of this, when the color transmissible filters 78R, 78G, and 78B of the rotatable filter 78 are interposed on the optical axis 162, the concave lens 158 is withdrawn by the solenoid 174 for realizing a rotational motion for the purpose of compensate light reduction due to the fact that the illuminating light passes through the color filters 78R, 78G, and 78B by way of focusing the illuminating light on the end surface of the light guide 63 by means of the convergence lens 79. On the other hand, when the rotatable filter 78 is withdrawn from the optical axis 162, the illuminating light is defocused on the end surface of the light guide 63 by interposing the concave lens 158 on the optical axis 162 for the purpose of preventing the end surface of the light guide 63 from being burned.

When the fiber scope 102B to which the external TV camera 105 is connected is connected as illustrated, the output signal from the SID 97 is converted into brightness signal Y and color difference signals R-Y and B-Y by means of the preprocess circuit 112, and is input to the frame memory 122 via a switch 121 which is controlled by the movement control mechanism 118. The signals read from the frame memory 122 are input to a post process circuit 123 at which it is converted into a NTSC type of combined image signal and signals representing the three primary colors, red, green and blue, and output to the monitor through each of output terminals 124 and 125.

If the frame memory 122 is, similarly to the second embodiment, provided with a means for supplying a freezing signal, a freezing image can be realized.

On the other hand, when the light guide connector receiver and the signal connector receiver 113A of the video processor 111 are connected with the light guide connector 115 and the signal connector 114 of the electronic scope 102A, the movement control circuit 118 detects the fact that the connector 114 is connected, and moves the rotatable filter 78 and the motor 77 downwardly as shown in FIG. 7 in order to interpose the rotatable filter 78 on the illuminating light passage, and switches the switch 121 in such a manner that the upper contact is conductive with electricity. In this state, the driver 131 supplies a driving signal to the SID 67 so as to make the SID 67 output an imaging signal. This signal is input to the plane sequential preprocess circuit 132 via the preamplifier 84. This preprocess circuit 132 includes an A/D converter, a frame memory, add a D/A convertor (omitted from the illustration), and synchronizes the thus-input plane sequential signal so as to input it in the form of signals each representing red, green, and blue. The thus-output signals are input to a matrix circuit 133. This matrix circuit 133 converts the signals into brightness signal Y, color difference signals R-Y, and B-Y, the signals then being input to the frame memory 122 via the switch 121. In front of the frame memory 122 and behind the same is, in actual, respectively provided with an A/D converter and a D/A converter, however they are omitted from FIG. 5.

The condition of the rotation of the above-described rotatable filter 78 is grasped by a timing control circuit 135 to which the output signal from the sensor 88 is input. The timing control circuit 135 control the timing of the driver 131, preprocess circuit 132, matrix circuit 133, frame memory 122, and the postprocess circuit 123.

The operation and effect of the third embodiment are similar to those obtained by the above-described second embodiment. Furthermore, an advantage can be obtained in this embodiment in that in a case of use of the fiber scope 102B alone, the video processor 111 can supply white light for fiber scopes, therefore, it can be used as a light source for fiber scopes.

Figure 9:
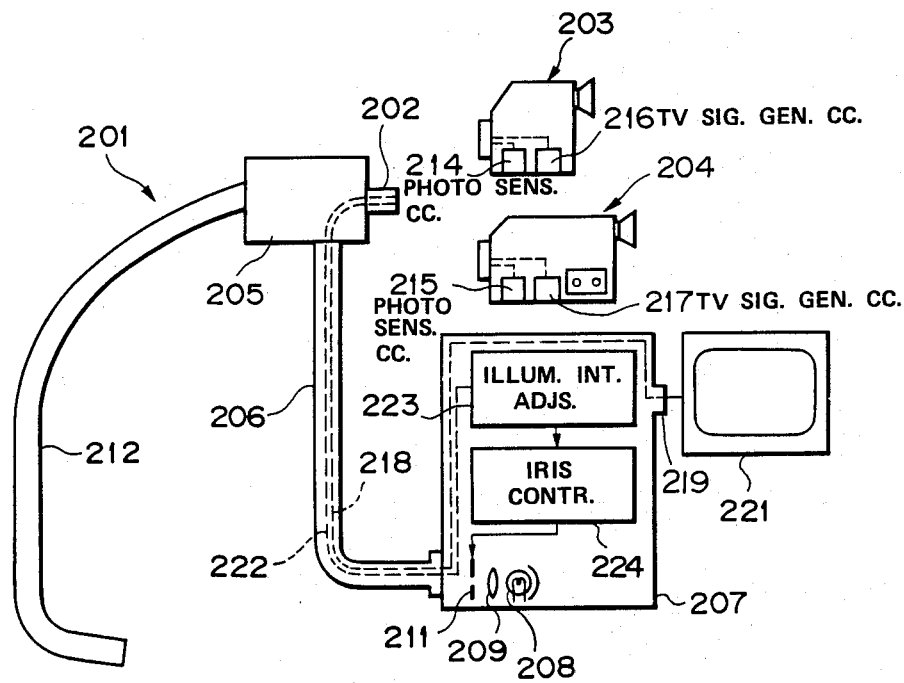
FIG. 9 illustrates the structure of a fourth embodiment of the present invention.

Meanwhile, in the conventional example, a still camera or an ocular type of TV camera are connected to the fiber scope. In the case of the still camera, the endoscope image photographed cannot be immediately realized, while in the case of the ocular type of TV camera, a filing device or the like is needed to be installed, causing the size of the system to become enlarged. In order to overcome these problems, the ocular portion 202 of the fiber scope 201 may be, as shown in FIG. 9, arranged to be able to mount an electronic camera 203 or a VTR included type of camera 204 for the purpose of recording the images obtained by an endoscope with a compact camera (that is, the electronic camera 203 or the VTR included type of camera).

A universal cable 206 is extended from a handling portion 205 of the above-described fiber scope 201. By connecting this universal cable 206 to a light source device 207, the illuminating light emerged from a light source lamp 208 is supplied, via a convergence lens 209 and an aperture 211, to a light guide (omitted from the illustration). As a result of this, the illuminating light is transmitted through the light guide, and is emerged from the front end surface of the insertion portion 212 for the purpose of illuminating the object. The image of the object is imaged on an image guide by an object lens (omitted from the illustration), and the image guide transmits the image to the ocular portion 202.

The above-described ocular portion 202 is arranged to detachably mount the electronic camera 203 or the VTR included type of camera 204. Each of the electronic camera 203 and the VTR included type of camera 204 includes corresponding photometry circuits 214 and 215 and TV signal outputting circuits 216 and 217. As a result of this, when the electronic camera 203 or the VTR included type of camera 204 is mounted to the ocular portion 202, the optical image transmitted through the image guide is photographed, is converted into an image signal, is transmitted to a light source device 207 via a TV signal cable 218 in the universal cable 206, and is output to a monitor 221 through the outputting terminal 219.

A photometry signal from a photometry circuit 214 or 215 is input to a dimmer circuit 223 in the light source device 207 via a photometry signal transmitting cable 222 in the universal cable 206. The dimmer circuit 223 detects the quantity of illuminating light used to photograph the image, sends a signal corresponding to the quantity of illuminating light to an aperture control circuit 224, and controls the degree of aperture of the aperture 211 in order to control the quantity of illuminating light in such a manner that a proper illuminating light is obtained with respect to the imaging device.

Figure 10:
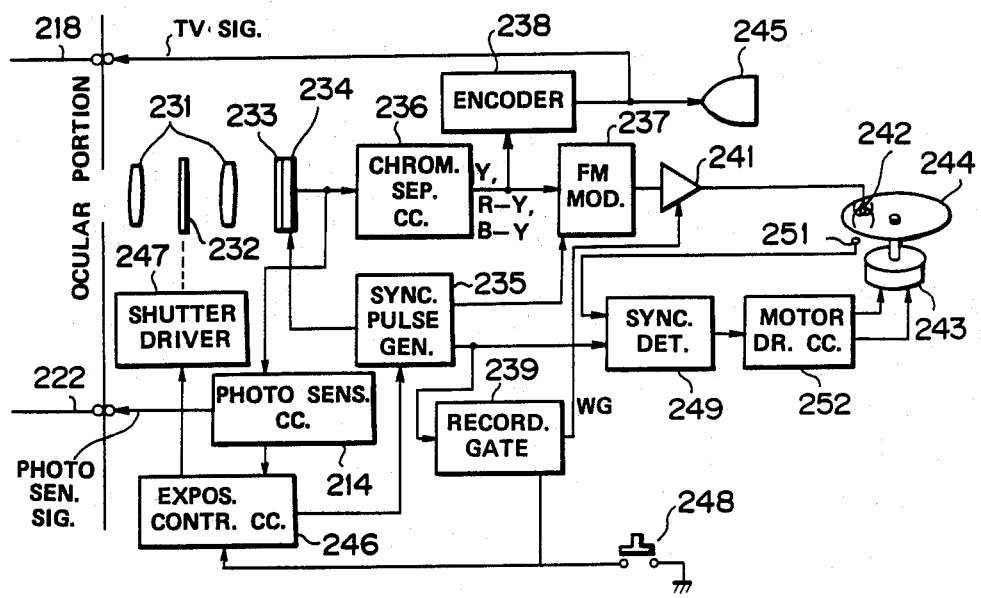
FIG. 10 illustrates the structure of an electronic camera forming the fourth embodiment.

The structure of the above-described electronic camera 203 will now be described with reference to FIG. 10.

An imaging lens system 231 is disposed in such a manner that it confronts an ocular lens (omitted from the illustration) in the ocular portion 202. An element shutter 232 is interposed during the imaging lens system 231. On the focusing plane of the imaging lens system 231 is provided with a color dividing filter 233 and a CCD 234. A driving signal is supplied from a synchronous pulse generating circuit 235 to this CCD 234, as a result of which, an imaging signal which has been accumulated as charge is output from the CCD 234. The output signal from the CCD 234 is divided into brightness signal Y, color difference signals R-Y and B-Y by a color dividing circuit 236, and the thus-divided signals are output. Then, they are input to an FM modulator 237 and an encoder 238. By means of the FM modulator 237, they are FM-modulated, and are supplied to a magnetic head 242 via a buffer 241 (write state) which is controlled in such a manner that it is arranged to be brought to a conductive state in response to a write gate signal WG output by a record gate circuit 239. Consequently, they are recorded on a magnetic disk 244 whose motor 243 is rotated by this magnetic head 242.

On the other hand, the signal input to the above-described encoder 238 is converted into a TV signal, is displayed on a view-finder monitor 245, and is able to be displayed also on an external monitor 221 via a cable 218 in the ocular portion 202 and the universal cable 206.

The output signal from the CCD 234 is input to a photometric circuit 214 so that a photometric signal is output. This photometric signal is input to an exposure control circuit 246 in which it supplies a signal to a shutter driver 247 when the exposure reaches a proper level in order to realize a state in which the element shutter 232 prevents light transmission. A shutter button 248 is connected to the exposure control circuit 246 so that the element shutter 232 is switched on in response to the fact that the shutter button is pressed. As a result of this, photographing is started, and simultaneously, a trigger signal is output to a synchronous pulse generator 235 which thereby output a synchronous signal which corresponds to the operation of the shutter.

The above-described synchronous pulse generator 235 opens the element shutter 232 in order to output a driving signal for reading when the CCD completes its charge storing operation, and supplies a synchronous signal which is in synchronization with the operation of the shutter button 248 to the FM modulator 237, synchronization detector 249, and the record gate circuit 239 so that a timing pulse signal for recording action is output. The synchronization detector 249 detects the difference in phase between the output signal from a rotation detecting sensor 251 disposed opposite to the magnetic disk 244 and a pulse of the synchronous pulse generator 235, and supplies a driving signal which corresponds to the difference to the motor driving circuit 252 in order to control the motor 243 to be rotated at a constant speed without occurrence of phase difference.

The photometry signal is input to the light source device 207 via the cable 222 in the ocular portion 202 and the universal cable 206 in order to control the quantity of the illuminating light.

Figure 11:
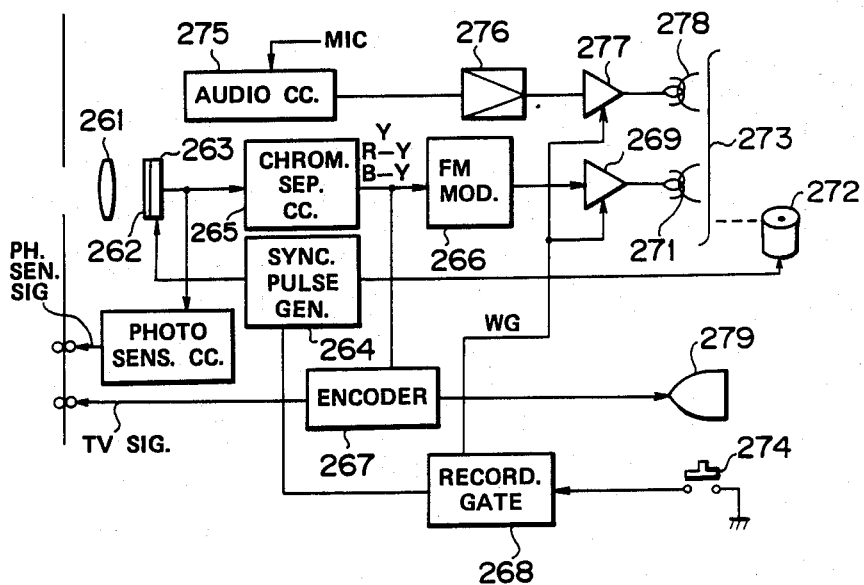
FIG. 11 illustrates the structure of a VTR included type of camera forming the fourth embodiment.

The structure of the VTR included type of camera 204 is shown in FIG. 11.

The optical image which has been transmitted through the image guide is focused on a CCD 263 by an object lens 261 via a color dividing filter 262. A driving signal is supplied to the CCD 263 from a synchronous pulse generator 264, and the signal read from the CCD 263 is input to a color dividing circuit 265 wherein it is divided into brightness signal Y and color dividing signals R-Y and B-Y which are input to an FM modulator 266 and an encoder 267. The signal which has been FM-modulated by the FM modulator 266 is input to an imaging head 271 via a buffer 269 which is arranged to be opened by a recording gate signal WG which is output by a record gate circuit 268, and is recorded by a tape 273 which is moved by a tape rotating motor 272.

The record gate circuit 268 is brought to an operative state by the operation of an audio recorded/image record button 274.

When the above-described button 274 is pressed, a timing signal is input to the synchronous pulse generator 264 via the record gate circuit 268, the timing signal outputting a synchronous pulse. In synchronization with this timing signal, the ensuing image and audio recording operations are determined. As a result of this, an audio signal which is input through a microphone (omitted from the illustration) is input to an audio circuit 275, is compensated in its frequency characteristics and amplified, is further amplified by an amplifier 276, and input to an audio head 278 via a buffer 277. As a result of this, it is recorded on the tape 273.

On the other hand, the signal imaged by the CCD 263 is divided in its color by the color dividing circuit 265, and is simultaneously input to the photometry circuit 215 so that a photometry signal is output. As a result of this, the thus-color divided signal is FM modulated, and the scope image is recorded on the tape 273 by the image head 271 and the audio recording head 278.

The thus-color divided signals also input to the encoder 267, converted into a TV signal, displayed on the external monitor 221, and also displayed by a viewfinder monitor 279.

The above-described photometric signal is input to the dimmer circuit 223 via the cable 222 in the ocular portion 202 and the universal cable 206, and acts to control the degree of aperture of the aperture 211 in order to adjust the quantity of the illuminating light to a proper level.

According to this embodiment, since a TV signal can be supplied to the monitor 221 via the universal cable 206 of the scope 201 and the light source device 207, operationality can be improved. Furthermore, the endoscope image can be recorded or reproduced even if the size of the apparatus is small.

In this embodiment, the TV signal can solely be transmitted to the light source device so as to be dimmed.

Figure 12:
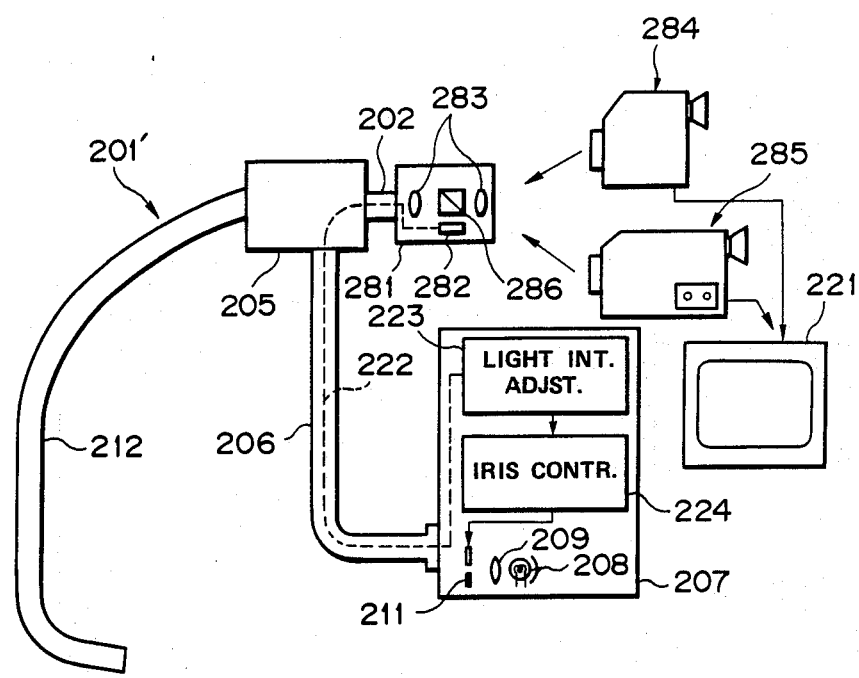
FIG. 12 illustrates the structure of a fifth embodiment of the present invention.

Although in this embodiment, an example is shown in which an electronic camera or a VTR included type of camera used exclusively in an endoscope is employed, a common type of electronic camera 288 or a common type of VTR 285 may be connected by arranging the structure, as shown in FIG. 12, in such a manner that an intermediate barrel 281 is connected to the ocular portion 202, and a photometry circuit 282 and a conversion lens system 283 are accommodated in the intermediate barrel 281. The photometry circuit 282 branches into a transmitted light used for photographing and a reflection light used for photometry by a half mirror 286 interposed during the conversion lens system 283.

In this state, the fiber scope 201 is passed through only by the photometry cable 222, therefore, the TV signal is transmitted from each of the TV signal outputting terminals of the electronic camera 284 or the VTR included type of camera 285 to the monitor 221 through a cable connected to the TV signal input terminal of the monitor 221.

As described above, according to each of the above-described embodiments, the operationality can be improved since the signal cable through which the signal is transmitted between the imaging means such as TV camera mounted on the ocular portion of the fiber scope and a signal processing means for processing the signal input to the imaging means is disposed in the fiber scope, and thereby any cable is not needed to be connected to the imaging means such as TV camera.

Figure 13:
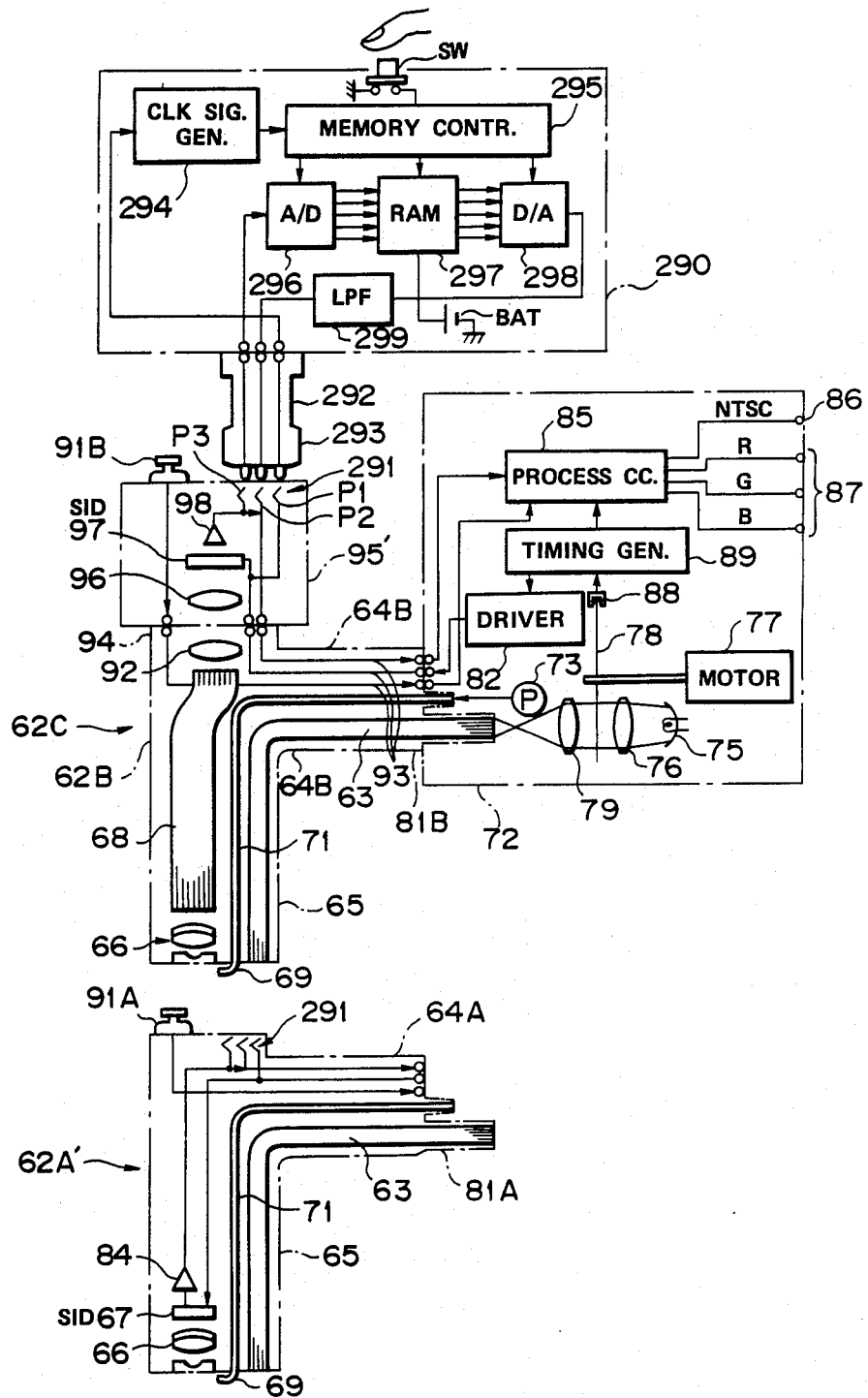
FIG. 13 illustrates the structure of a sixth embodiment of the present invention.
Figure 15:
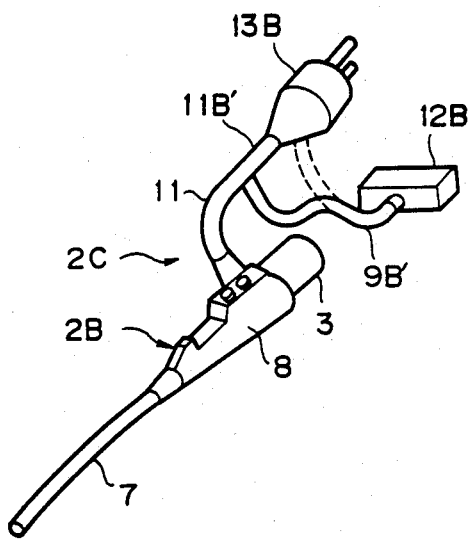
FIG. 15 is a perspective view of a fiber scope according to a modified example of the first embodiment of the present invention.

FIG. 13 illustrates a system according to a sixth embodiment of the present invention.

The sixth embodiment is so constituted that a semiconductor memory device 290 can be used by connecting to the apparatus shown in the second embodiment shown in FIG. 5.

A TV camera 95' is provided on its, for example, upper surface (rear side), with a connector receiver 291. It is arranged that this connector receiver 291 and a connector 293 fitted to an end portion of an cable 292 extended from the semiconductor memory device 290 can be connected.

The above-described TV camera 95' is the same as that shown in the second embodiment when the above-described connector 293 is not connected, but when this connector 293 is connected, pin receivers P2 and P3 of the connector receiver 291 are turned off. In this state, an SID driving signal supplied to the SID 97 is input to a clock signal generator 294 so that a clock signal for memory is generated in response to the SID driving signal, and is input to a memory controller 295.

The output from the preamplifier 98 is converted into a digital signal by an A/D converter 296, and is input to a RAM 297. This RAM 297 comprises, for example, a dual port type of RAM which can individually conduct writing and reading. Therefore, writing is conducted via the A/D converter 296, a data one frame before the written position is read out, is returned to an analog signal by a D/A converter 298, and is input to the process circuit 85 via an LPF 299 for eliminating noise due to quantization.

The above-described memory controller 295 is arranged to generate a conversion clocks for the A/D converter 296 and the D/A converter 298 in response to the clock signal from the clock signal generator 295, or generate an address signal of the RAM 297.

This RAM 297 has a capacitance of, for example, three frames red, green, and blue. It stops, by means of a writing command switch provided for the semiconductor memory device 290, writing data in prior to this switching-on of the writing command switch. As a result of this, image data corresponding to the three frames red, green, and blue (one color frame) in prior to the switching-on of the writing command switch can be maintained. The semiconductor memory device 290 includes a battery BAT so that the image data stored in the RAM 297 can be maintained with the aid of this battery BAT.

The electronic scope 62A' is also provided with a connector receiver 291 in order to connect the semiconductor memory device 290, and store the image data in the RAM 297.

Figure 14:
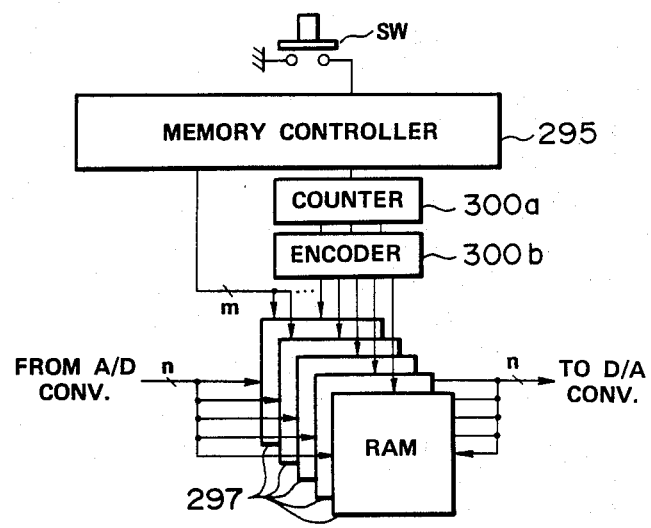
FIG. 14 is a block diagram illustrating an essential portion of a modified example of the sixth embodiment.

In this sixth embodiment, image data corresponding to three frames red, green, and blue (one color frame) can be stored, the structure may be arranged in such a manner, as shown in FIG. 14, that a plurality of color frames can be stored by providing a multiplicity of RAMs 297. The multiplicity of RAMs 297 realizes a fact, by using a counter 300a and an encoder 300b, that the image data can sequentially be stored in the different RAMs in accordance with the number of switching on/off of the switch SW.

Although, in FIG. 13, the semiconductor memory device 290 is arranged to be capable of being connected to the TV camera 95' or the electronic scope 62A' with the use of the cable 292, the semiconductor memory device 290 may be directly connected to the TV camera 95' or the electronic scope 62A without use of the cable 292.

Although in the first embodiment shown in FIG. 4, two universal cables 9B and 11B are extended from the fiber scope 2B, the structure may be arranged in such a manner that a single universal cable 11 is extended from the handling portion 8, and is branched at the intermediate portion thereof into two cables 9B' and 11B'. On the other hand, a connector 12A may be provided by extending, as shown by dashed line, a cable from the side portion of the connector 13B.

Figure 16:
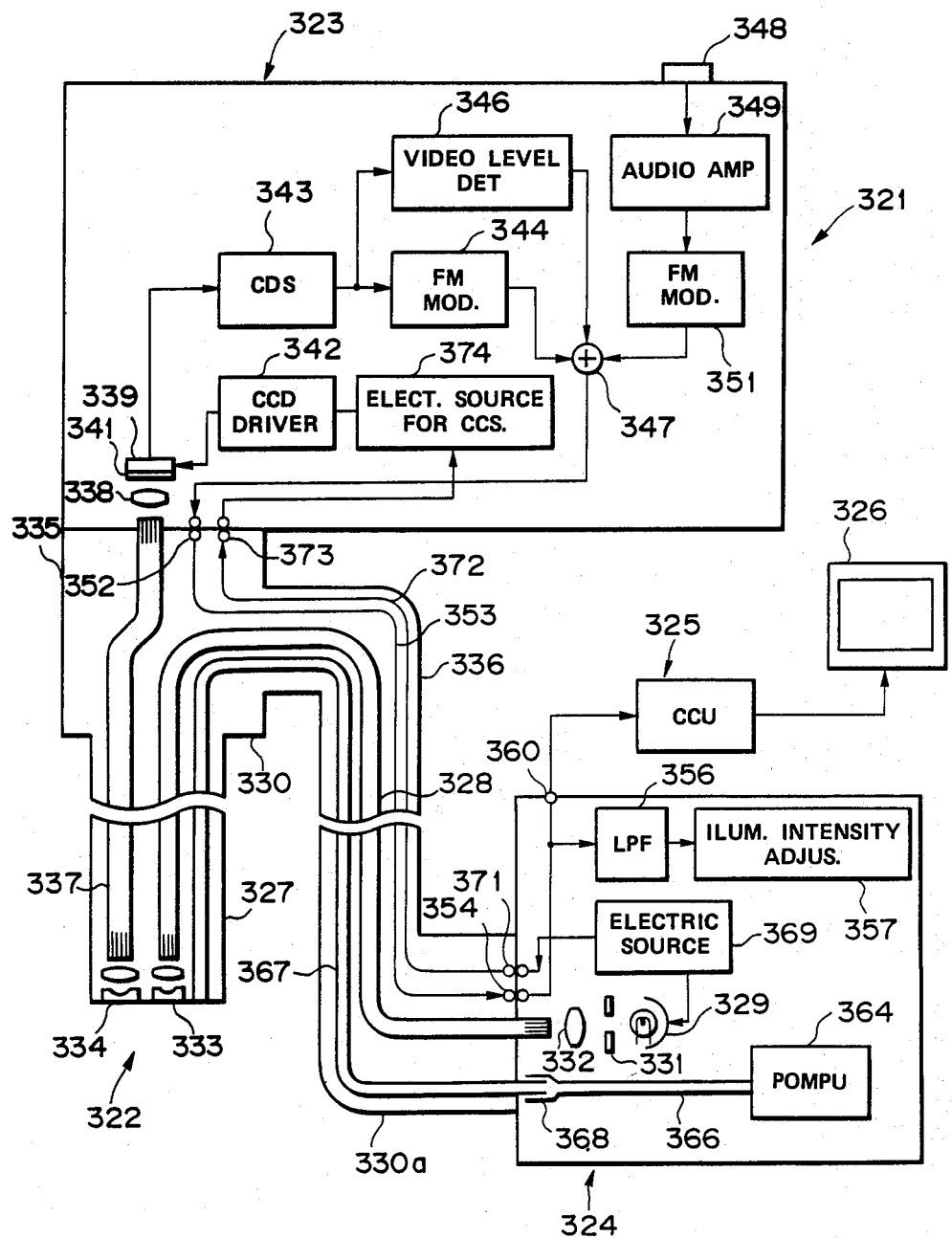

As shown in FIG. 16, an endoscope device 321 according to a seventh embodiment of the present invention comprises a fiber scope 322, an external TV camera 323 connected to this fiber scope 322, a light source device connected to this fiber scope 322, and adapted to supply illuminating light, a camera control unit 325 connected to this light source device 324, and adapted to conduct signal processing, and a TV monitor 326 for displaying the image signal output by the camera control unit 325 (abbreviated as "CCU" hereinafter).

The above-described fiber scope 322 includes an elongated insertion portion 327, a handling portion 330 with a thick diameter which is connected to the rear portion of the insertion portion 327, and a universal cable 336 extended from the side portion of the handling portion 330 with a thick diameter.

The above-described insertion portion 327 and the universal cable 336 are passed through by a light guide 328 through which illuminating light is transmitted. By connecting a connector portion 330a disposed at the front end of the universal cable 336 to a light source device 324, white light emerged from a light source lamp, for example, a xenon lamp or the like, is arranged to be converged and made incident upon the incidental end surface of the light guide 328 by means of a condenser lens 332 after the white light has been adjusted in its quantity of light by a light shield member 331 for dimming. The illuminating light is transmitted through the light guide 328 to the light emerging end surface at the front end of the insertion portion 327, and is emerged toward the object via a light distribution lens 333. The object which has been illuminated with the illuminating light is arranged to be imaged, by an object lens 334, at the incidental end surface of the image guide 337 which passes though the insertion portion 327. The light emerging end surface of the image guide 337 is disposed opposite to an imaging lens 338 of an external TV camera 323 detachably connected to an ocular portion 335 disposed at the rear end of the handling portion 330, The thus-transmitted optical image is imaged by means of this imaging lens 338 on an imaging surface of a solid imaging device 339 (abbreviated as "CCD" hereinafter). On the imaging surface of this CCD 339, mosaic filters 341, for example red, green, and blue are provided.

The above-described CCD 339 outputs a frame signal (an image signal) which has been photoelectrically converted due to the supply of a drive signal from a CCD drive circuit 342 in the external TV camera 323. The image signal is input to a CDS (Correlation Double Sampling circuit) 343 in the external TV camera 323, in which it is applied with a double sampling, and 1/f noise or the like generated from the CCD 339 is controlled. The output from the CDS circuit 343 is an image information signal which is arranged to be FM-modulated by an FM modulator 344 as a modulation means after it has been input to the FM modulator 344. The image signal which has been FM modulated is arranged to be input to a mixer 347 as a mixing means.

Figure 17:
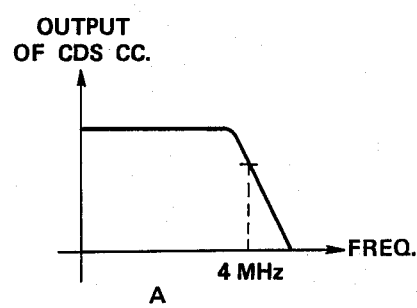

FIG. 17 is a spectrum drawing of an image signal output from the CDS circuit 343, the image signal being a signal with a frequency component of substantially 4 MHz from a DC in this embodiment.

The image information signal from the CDS circuit 343 is also input to an image level detection circuit (abbreviated as "DET" hereinafter) 346 in which the image signal output from the CDS circuit 343 is detected, and is converted into a DC signal the level of which corresponds to the photoelectrically converted output level from the CCD 339. This DC signal is input in the form of an automatic dimming signal to the above described mixer 374 wherein it is mixed with the above described image signal. The output from the FM modulator 344 does not include a DC component since it is modulated, therefore, problems such as interference or the like are not arisen if a DC component of the automatic dimming signal is mixed.

The external TV camera 323 is provided with a microphone 348 through which voice of an operator can be input. The output of the microphone 348 is amplified by an audio-amplifier 349, and is input to an audio FM modulator 351 used exclusively for an audio wherein it is FM modulated. The FM wave output from the audio FM modulator 351 is input to the above-described mixer 347.

Figure 18:
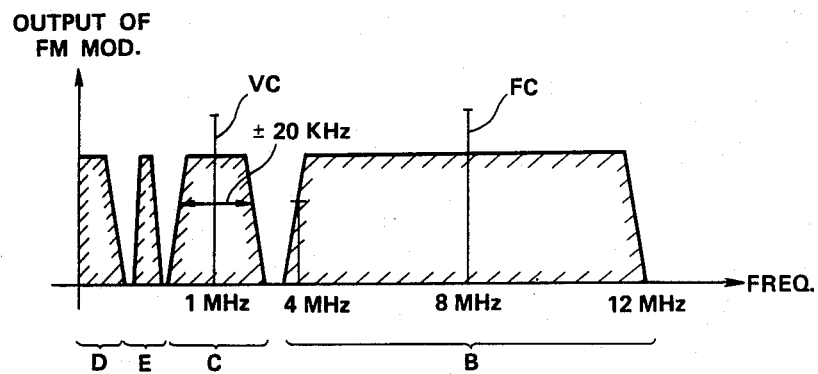

FIG. 18 is a spectrum drawing of the output from the mixer 347.

The FM wave with the frequency band B is the spectrum drawing of the FM modulator 344. Since, in this embodiment, the frequency FC of the carrier wave is set to 8 MHz, a side band of 8 MHz±4 MHz is generated. The signal with the frequency band of B has been FM-modulated, any DC component is not, of course, included. The FM wave with the frequency band of C is the output spectrum drawing of the audio FM modulator 351. In this embodiment, the frequency VC of the carrier wave is 1 MHz, a side band of ±20 KHz is contained. Therefore, the frequency band does not overlap the FM wave for the image signal, and jamming due to interference does not occur. The FM wave with the frequency band of D is a spectrum drawing of the automatic dimming signal, and is an output spectrum drawing of DET 346. As described above, the automatic dimming signal includes a DC component. In this embodiment, it is ranged between 0 (DC) to 100 Hz, therefore, jamming does not also occur to the FM wave and image FM wave.

The output from the above-described mixer 347 is transmitted to a signal cable 353 which passes through the handling portion 330 and the universal cable 336 via a connector pin 352 which is disposed opposite to the ocular portion 335, and which can mount and connect the external TV camera 323 to the fiber scope 322. This signal cable 353 is connected to a connector pin 354 provided for the connector portion 330a so that the connector portion 330a is connected to the light source device 24 and simultaneously, FM wave can be input to a low-pass filter (abbreviated as "LPF" hereinafter) disposed in the light source device 324. The cutoff frequency of the LPF 356 is arranged to act to separate and extract the range between 0 to 100 Hz of the frequency range D shown in FIG. 18. The thus-extracted automatic dimming signal is arranged to be input to the dimming circuit 357. This dimming circuit 357 is arranged to control the dimming light shield member 331 in order to adjust the quantity of illuminating light.

In the light source device 324, a power source circuit 369 is provided. This power source circuit 369 supplies power to the light source lamp 329, and is connected to a signal cable 372 passing through the universal cable 336 and the handling portion 330 via a connector pin 371 provided for the connector portion 330a. This signal cable 372 is connected to a circuit power source 374 which supplies power to the electric parts in the external TV camera 323 via a connector pin 373 provided for the ocular portion 335 so that power is supplied.

The FM wave which has been input to the light source device 324 is input to the above-described LPF 356, and is branched in order to be output to the CCU 325 via the connector pin 358.

The structure of the CCU 325 will now be described with reference to FIG. 19. The FM wave to be input to the CCU 325 is input to a high pass filter (abbreviated as "HPF" hereinafter) 358 and a band pass filter (abbreviated as "BPF" hereinafter) 359. In this HPF 358, the image FM wave shown in the frequency range B shown in FIG. 18 is separated and extracted. The thus-extracted image component is input to an image demodulator 361, and an image signal is demodulated. The thus-demodulated image signal is input to an image processing circuit 362, and in which a synchronous signal is added, and a color signal processing is conducted. As a result of this, for example, an NTSC combined image signal is output. On the other hand, the BPF 59 separates and extracts the frequency range C showing the audio FM wave shown in FIG. 18. The thus extracted audio component is input to an audio demodulator 363. This audio demodulator 363 demodulates and outputs an audio signal. The above-described NTSC combined image signal and an audio signal are input to a TV monitor so that the image of the object is displayed and the voice is reproduced.

The light source device 324 includes an air supply and intake pump 364. A conduit run 366 connected to the air supply and intake pump 364 is detachably connected with a conduit run 367 which passes through the insertion portion 327 and the universal cable 336 and a connecting portion 368 provided for the connector portion 330a. As a result of this, the front end surfaces of the light distribution lens 333 and the object lens 334 are washed or the object is washed.

As the signal cable 353 for transmitting the image signal employed in this embodiment, a signal cable for controlling dimming of the external camera (the structure is different from that shown in FIG. 16) may be utilized, or the signal cable 372 for supplying power to the automatic dimming circuit of the external camera may be used for the cable for supplying power to the circuit power source 374 shown in FIG. 16. As a result of this, a fiber scope including these signal cables 353 and 372 can be as it is used. In this case, in the prior art, a cable for signal processing is needed to be extended from the TV camera. According to this embodiment, the image signal is mixed and transmitted through the signal cable 353, and the cable is not needed to be extended outwardly from the TV camera 323. Therefore, the cable does not interrupt the handling. That is, operationality is significantly improved.

FIG. 20 illustrates an endoscope according to an eighth embodiment of the present invention.

The external TV camera 323 which is detachably connected to the ocular portion 335 of the fiber scope 322 is provided with a press button type of switch 377 which outputs a command signal representing the start of recording or track transportation of the peripheral equipments, for example, VTR, video disk, photographing device. When this press button switch 377 is operated by an operator, an electric switch portion 379 is turned on or off so that its signal is input to the FM modulator 381. In accordance with the turning on/off of the electric switch 379, the output frequency of the FM modulator 381 is varied. The output from the FM modulator 381 is supplied to the mixer 347 shown in the seventh embodiment. As a result of this, the frequency spectrum drawing of the mixer 347 is arranged to be supplied with the frequency range E shown in FIG. 18. The thus mixed FM wave is input to the CCU 325 via the universal cable 336 and the light source device 324. The FM wave is input to the BPF 382 provided in the CCU 325. This BPF 382 separates and extracts only the frequency range E, and inputs the signal component to the demodulator 383. The command signal which has been demodulates by this demodulator 383 is reproduced and input to the output terminal 384 of the CCU 325. A VTR 386 and a video disk 387 are connected to the output terminal 384. The command signal input is used for, for example, a recording trigger signal or a track transporting signal.

According to the present invention, an operator 387 can easily control the peripheral equipments by mixing the control signal which can control the peripheral equipments with the FM wave.

The other structure and the effect are the same as those of the seventh embodiment.

In each embodiments described above, the FM signal modulated in response to the image signal, audio signal and control signal is mixed with the dimming control cable for the purpose of transporting it. However, it may be mixed with the signal cable 372 for circuit power source. In this case, the separation and extraction of the FM wave are conducted by means of a BPF and LPF. The signal cable 372 is connected to the light source device 324 or the CCU 325 which are provided with BPF and LPF.

Although, in the above described seventh and eighth embodiments, a case is described in which an external TV camera is connected to the fiber scope, the former is not limited to be fitted to the fiber scope, it may be fitted to a hard endoscope. Furthermore, the modulation may be conducted in an AM or PCM manner.

Figure 21:
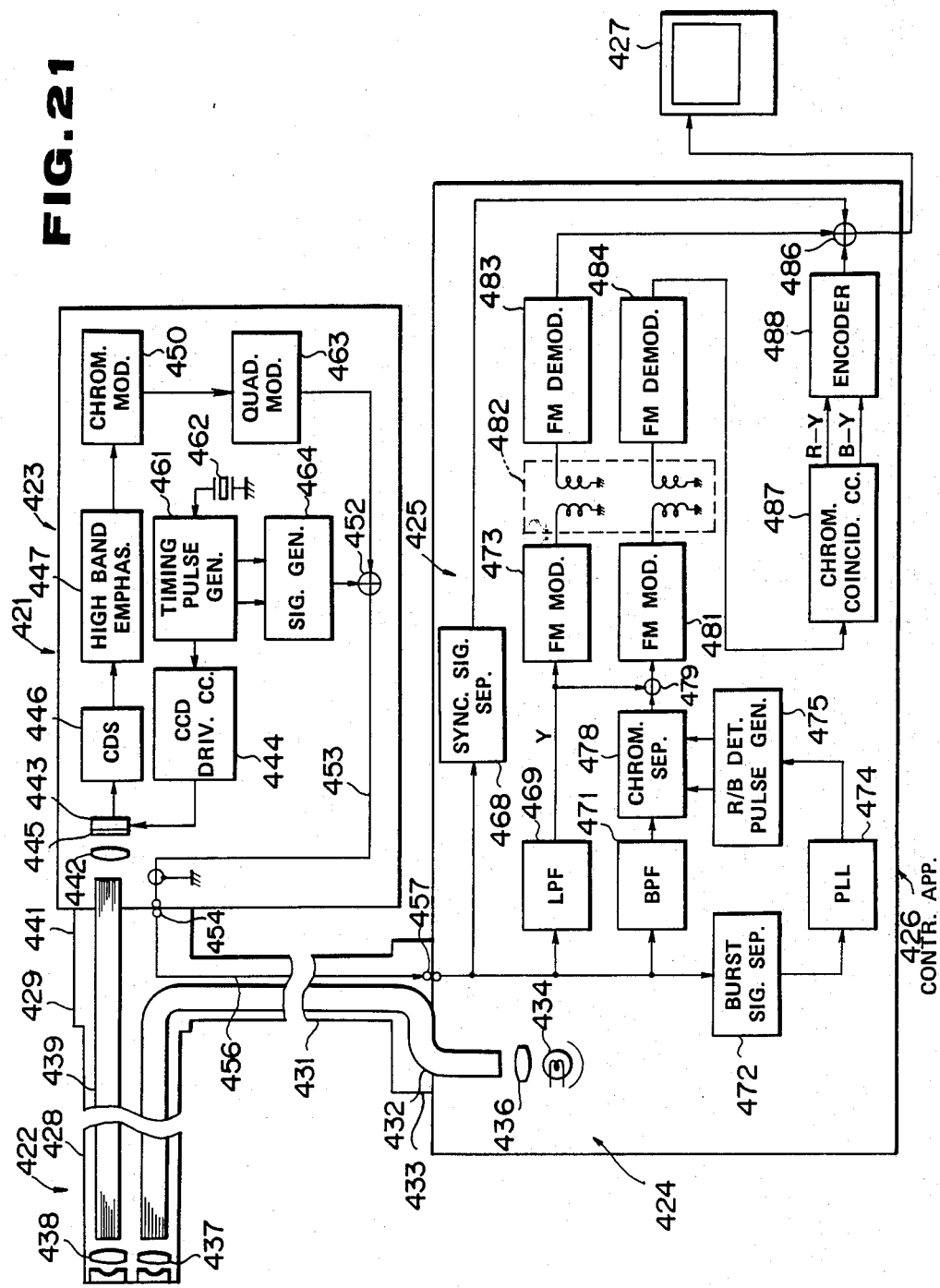

As shown in FIG. 21, an endoscope 421 according to a ninth embodiment comprises a fiber scope 422, an external TV camera 423 connected to the fiber scope 422, a control device 426 which includes a light source portion 424 connected to the fiber scope 422 in order to supplying illuminating light and an image signal processing portion 425 for image-processing an image signal transmitted from the external TV camera 423, and a TV monitor 427 for displaying the image signal output from the control device 426.

The above described fiber scope 422 comprises an elongated insertion portion 428, a handling portion 429 with a large diameter connected to the rear portion of the insertion portion 428, and a universal cable 431 extending from the side portion of the handling portion 429 with a large diameter.

The above-described insertion portion 428 and the universal cable 431 are passed through by a light guide 432 formed by a fiber bundle for transmitting illuminating light. By connecting a connector portion 433 at the front end of the universal cable 431 to the light source portion 424, white light emerged from a light source lamp 434 such as a xenon lamp is arranged to be converged by means of a condenser lens 436 on the incidental end surface of the light guide 432. The illuminating light is transmitted to the emerging end surface at the front end portion of the insertion portion 428 through the light guide 432 so that the object is lighted via the light distribution lens 437. The image of the object is arranged to be imaged on the light incidental end surface of an image guide 439 formed by a fiber bundle passing through the insertion portion 428. The light emerging end surface of the image guide 439 is positioned opposite to the imaging lens 442 of the external TV camera 423 which is detachably connected to the ocular portion 441 provided at the rear end of the handling portion 429. The optical image which has been transmitted by the imaging lens 442 is imaged on the imaging surface of a solid imaging device (abbreviated as "CCD" hereinafter) 443 as an imaging means. The imaging surface of the CCD 443 is provided with a mosaic filter 445 of, for example, red, green, and blue.

The above described CCD 443 outputs a frame signal (image signal) which has been photoelectrically converted due to the application of the drive signal from a CCD driving circuit 444 in the TV camera 423. The image signal is input to a CDS (Correlation Double Sampling) circuit 446, and is applied with the double sampling, and 1/f noise or the like generated in the CCD 443 is controlled.

FIG. 22 is a frequency spectrum drawing of the output of the CDS circuit 46. The brightness signal 448 has the frequency component of substantially 3 MHz. The carrier wave 451 of the carrier color signal 449 is 8 MHz, and the carrier color signal 449 has the range of 8 MHz±500 KHz.

The output from the above-described CDS circuit 446 is input to a high band emphasizing circuit 447 so that the high band component of the frequency is emphasized, and is input to a color dividing circuit 450 wherein a brightness signal Y and color difference signals R-Y and B-Y are generated. These signals are input to a quadrangle modulator 463. By this quadrangle modulator 463, the color difference signals R-Y and B-Y are quadranglarly modulated by a color carrier wave, and are mixed with the brightness signal Y. The thus-mixed signal is arranged to be output to a transmitting cable 453 via a mixer 452. This transmitting cable 453 is arranged to be connected by a terminal 454 to a transmitting cable 456 which passes through the above-described universal cable 431. This transmitting cable 456 is furthermore arranged to be connected to each circuit provided in the control device 426 by a terminal 457.

As the light source lamp 434 for an endoscope, for example, a xenon lamp is employed. This lamp 434 is, in principle, a discharge lamp, therefore, it generates exceeding level of noise. Furthermore, since the light source portion 424 comprises a variety of electrical circuits, exceeding level of noise is generated too. The noise due to the above-described parts are mixed with the transmitting cables 453 and 456, as a result of which, the S/N ratio of the image signal obtained by the CCD 443 is exceedingly deteriorated. Referring to FIG. 23, it is easy for noise 458 from air to be caught by the transmitting cables 453 and 456 when the frequency becomes high. Therefore, in order to eliminate the affection of the noise, the high band component of the signal transmitted may be raised to the characteristics of frequency shown in FIG. 23. The high band emphasizing circuit 447 is provided for the purpose of achieving it. A dashed line 459 of FIG. 23 designates a countermeasure against the noise mixture with the transmitting cables 453 and 456 by means of raising the high band region. This high band emphasizing circuit 447 is formed by, for example, a high bypass filter shown in FIG. 24.

Pulses such as vertical synchronous signal $\phi V$, horizontal synchronous signal $\phi H$, and a reset signal $\phi R$ which are generated by a timing pulse generating circuit 461 are input to the above-described CCD driving circuit 444, and are amplified in order to be supplied to the CCD 443. A reference clock signal output from a crystal oscillator 462 is arranged to be supplied to the timing pulse generating circuit 461. The horizontal synchronous signal and charge transmitting signal output from the timing pulse generator 461 are also output to the signal generator 464. FIG. 25a shows a horizontal synchronous signal which is to be input to the signal generator 464, and FIG. 25b shows a charge transmitting signal, which are made in synchronization with the period of transferring the charge. FIG. 25c shows a burst signal which is triggered by the horizontal synchronous signal, which is gated by a gate signal (omitted from the illustration), and which is a charge transporting signal generated in the burst shape. A waveform shown in FIG. 25d is arranged to be output from the signal generator 464 after the burst signal c and the horizontal synchronous signal a have been mixed. FIG. 25e shows the waveform output from the mixer 452 wherein the region at which the above-described burst signal is generated is set to be in, for example, the horizontal blanking period which is arranged in such a manner that it does not overlap a period 466 in which the image signal is generated. On the other hand, reference numeral 467 represents a color signal generated by way of mixture with the brightness signal.

FIG. 26 in detail shows the operating waveform of the charge transmitting signal shown in FIG. 25b. The period of the charge transmitting signal is aligned to the period of a picture element output from the CCD.

The image information signal output from the above-described mixer 452 is arranged to be input from the above-described terminal 457 to a synchronous signal separator 468, low-pass filter 469, band pass filter 471 and a burst signal separator 472. In the low-pass filter 469, the brightness signal 448 shown in FIG. 22 is separated and extracted, while in the band pass filter 471, the transmitting color signal 449 shown in the same figure is arranged to be separated and extracted. The brightness signal Y which has been separated by the low-pass filter 469 is input to an FM modulator 473.

The above-described burst signal separating circuit 472 separates and extracts the burst signal shown in FIG. 25c. The burst signal of the charge transmitting signal which has been separated and extracted is input to a PLL (phases synchronizing control loop) circuit 474. In this PLL circuit 474, the thus-input burst signal is converted into a continuous signal. The output from the PLL circuit 474 is input to a R/B detection pulse generating circuit 475, and is made a clock signal.

Figure 27:
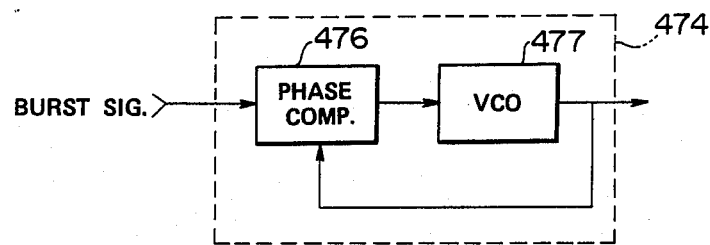

FIG. 27 shows a specific example of the PLL circuit 474, in which, the output from the burst signal separating circuit 472 is made one of the inputs of a phase comparator 476. The compared output from the phase comparator 476 controls the oscillation frequency of a voltage control oscillator (abbreviated as "VCO" hereinafter) 477. The output from the VCO 477 is arranged to be input to the other input terminal of the phase comparator 476. As a result of this, as the output from the VCO 477, a continuous signal whose phase is synchronized with the burst signal can be obtained, and the burst signal shown in FIG. 25c can be reproduced.

The above-described R/B detection pulse generating circuit 475 is arranged to generate and input R-detection signal and B-detection signal to a color separation circuit 478 which extracts the color difference signal in response to the transmitting color signal which has been separated by the above-described band pass filter 471.

FIG. 28 shows the relationship in phase between the R/B detection signal and the output from the CCD. In the output from the CCD, in order to alternately generate color signals R and B every other picture element with respect to the brightness signal, the R/B detection signal is completely aligns in its phase to the charge transmitting signal. The R-detection signal aligns to the central portion of the period at which the R-signal is generated, and the B-detection signal is aligned to the central portion of the period at which the B-signal is generated.

The output from the above-described separation circuit 478 is a linear sequential signal in which the R and B-signals are generated at every horizontal scanning line, this linear sequential signal being input to a subtractor 479. To this subtractor 479, the brightness signal Y is input, this brightness signal Y generating the color difference signals R-Y and B-Y. These color difference signals R-Y and B-Y are input to an FM modulator 481. In the FM modulators 473 and 481, the frequency range of the image signal input is set to 1 MHz to 10 MHz. The thus-modulated image signal is arranged to be input to the primary side of an isolation transformer 482 which is provided for the purpose of isolating the circuit on the patient side and the secondary circuit.

The band at which the isolation transformer 482 can work is limited to AC component, it cannot transmit the DC component. On the other hand, the image signal includes the component (20 Hz) which approximates DC, therefore it cannot transmit the image signal. In order to solve this problem, the frequency range of the image signal is set to 1 MHz to 10 MHz by means of the FM modulators 473 and 481, whereby its transmission can be conducted.

The secondary side of the isolation transformer 482 is provided with each of FM modulators 483 and 484, whereby the linear sequential signal of the brightness signal Y and the color difference signals R-Y and B-Y are demodulated. This brightness signal Y is arranged to be input to the mixer 486, and the linear sequential signal is arranged to be input to the color difference synchronizing circuit 87. In this color difference synchronizing circuit 87, the linear sequential color difference signal is synchronized, and the color difference signals R-Y and B-Y are generated. These color difference signals R-Y and B-Y are input to a color encoder circuit 488, is converted into a chromatic signal, and is input to the above-described mixer 486. In this mixer 486, this chromatic signal, the brightness signal Y, and a synchronous signal input from the synchronous signal separator 468 are mixed, and the thus-mixed signals are, in the form of a composite signal, output to the TV monitor 427.

In the case where three primary colors signals R, G and B are output, a reverse matrix circuit or the like is provided to which the brightness signal Y and the color difference signals R-Y and B-Y are input.

The horizontal synchronous signal may be a composite signal which as well including the vertical synchronous signal.

As described above, according to this embodiment, since the image information signal can be transmitted through the transmitting cable 456 which passes through the universal cable 431, any transmitting cable through which the image information is transmitted is not needed to be connected to the external TV camera. As a result of this, only by connecting the universal cable to the control device 426, photographing can be conducted. Furthermore, since the transmitting cables are disposed only in the universal cable 431, it is easy for an operator to handle the apparatus in comparison with the case in which a plurality of cables are provided.

In this embodiment, although the light source portion 24 and the image signal processing portion 425 are provided in the control device 426, a marketed light source device can be connected by way of individually providing the above-described two parts, as a result of this, cost reduction can be achieved.

Figure 29:
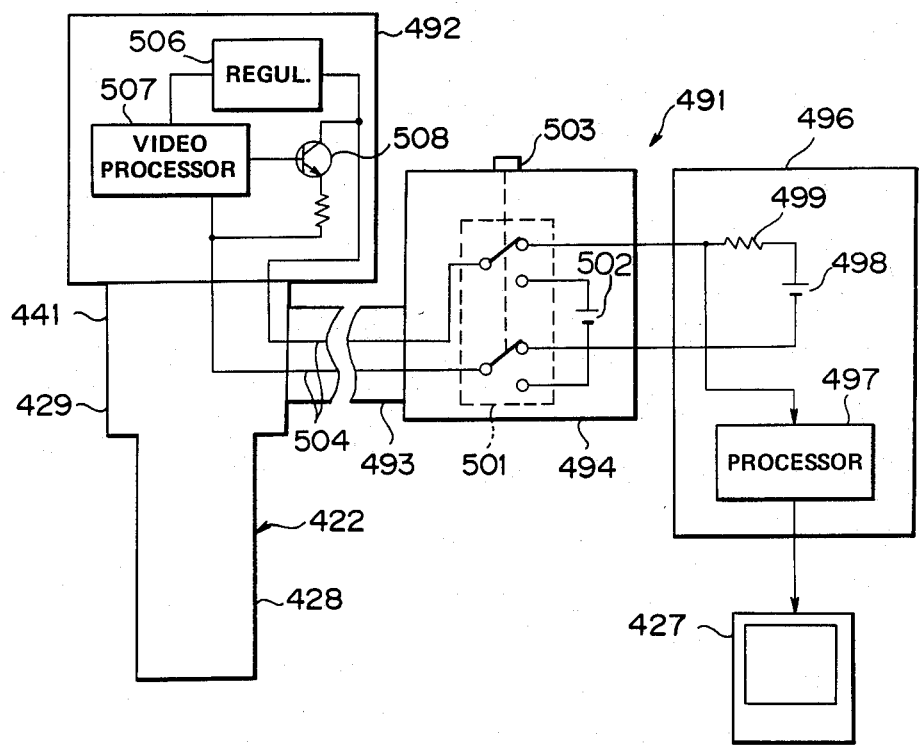
FIG. 29 is a schematic view illustrating the structure of a tenth embodiment of the present invention.

FIG. 29 illustrates the block diagram used for the whole body of an endoscope according to a tenth embodiment.

An endoscope 491 according to this embodiment comprises a fiber scope 22, an external TV camera 492 provided at an ocular portion 441 of the fiber scope 422, a light source device 494 which is connected with a universal cable 493 which is connected to the fiber scope 422, a control device 496 which is electrically connected to the light source device 494, and which conducts a signal processing, and a TV monitor 427 to which a combined video signal generated by the control device 496 is input, and which displays the image of the object.

The above-described control device 496 includes an image processor 497 and an external power source 498. The output from the external power source 498 is connected to one of the terminals of a switch 501 provided in the light source device 494 via a resistor 499. The other terminal of the switch 501 is connected to an internal power source 502 provided in the light source device 494. The external power source 498 and the internal power source 502 can be selected by, for example, manually handling this switch portion 503. The power source selected by the switch 501 is arranged to be supplied to a regulator 506 via a transmitting cable 504 passing through the universal cable 493. The power stabilized by the regulator 506 is arranged to be supplied to an image processor 507 formed by a CCD driving circuit or CCDs. This image processor 507 photoelectrically converts the image of an object obtained by the fiber scope 422, and outputs the thus photoelectrically converted image as an image information signal. This image information signal is input to a transistor 508, and electric current passing through the transistor 508 is modulated in response to the image information signal. When the electric current which has been modulated in response to the image information signal passes, voltage drop generates at the output terminal of the resistor 499 in the control device 496, and which represents the fact that the image information has been transmitted. This image information is input to the image processor 497, is converted into an NTSC type of composite signal or a RGB signal, and is displayed by a TV monitor 427.

According to this embodiment, since the image information is transmitted through the transmitting cable 504 which passes through the universal cable 493, and which supplies electricity, a transmitting cable through which image information is transmitted is not needed, therefore, the operationality of the endoscope 491 can be improved.

The other structure, operation and the effect are the same as those of the ninth embodiment.

Although in the fiber scope 102B shown in FIG. 7, a light guide 63 is employed which transmits the illuminating light, and which issues illuminating light through a light emerging end surface at the front end of the insertion portion 65, a fiber scope 520 may be employed which accommodates, as shown in FIG. 30, a lamp 521 at the front end portion of the insertion portion thereof. In this case, a power supplying cable 522 which supplies power to the lamp 521 is passed through the insertion portion 65 and the cable 522 extending from the rear end of the insertion portion 65, and is arranged to be connected to the power source of the lamp (omitted from the illustration). The other structure is the same as that of the fiber scope 102B.

On the other hand, in the electronic scope 102A shown in FIG. 7, as an alternative to the light guide 63, an electronic scope 532 may be employed in which a lamp 531 is, as shown in FIG. 31, accommodated at the front end of the insertion portion 65. In this drawing, the power supplying cable 533 passes through the cable 104A. In the same drawing, a synchronous type of color imaging means is formed by providing a mosaic color filter 534 at the front surface of the SID 67. If an LEDs are employed which emit light with each of wavelengths of red, green and blue, and sequentially lighting them, plane sequential type can be formed without the mosaic color filter 534.

For example, as an alternative to the signal cable 353 in the fiber scope 322 shown in FIG. 16, a light cable 551 shown in FIG. 32 may be used so as to form the fiber scope 552.

A camera 323' confronting the light incidental end surface 551a of the light cable 551 is provided with an LED 553, and it is driven in response to the modulation signal from the mixer 347. A phototransistor 554 is disposed in the light source device 324' in such a manner that it confronts the light emerging end surface 551b of the light cable 551, and its signal which has been photoelectrically converted is input to 325 and the LPF 353.

In this embodiment, the signal cable 372 comprises a electric wire, an optical cable may be employed for the purpose of transmitting light, and power generating force is generated due to a solar cell on the camera 323. This optical cable and the optical cable shown in FIG. 32 may be used commonly.

The optical cable shown in FIG. 32 may be, of course, applied to the other embodiments.

The other embodiments can be constituted by, for example, combining the above described embodiments.

What is claimed is:

1. An endoscope system comprising:
   an endoscope including an elongated insertion portion, light emergence means for issuing illumination light from a head of said insertion portion, an image guide having its incidence end inserted into said insertion portion and adapted to transmit an optical image, an ocular portion having an ocular window facing an emergence end of said image guide, a signal cable extending from a rear end of said insertion portion or from said ocular portion to the outside and provided with signal transmission line(s) inserted into said signal cable, a signal connector receiver provided on said ocular portion and connected to one end of said signal transmission line(s), and a signal connector attached to a head of said signal cable and connected to the other end of said signal transmission line(s);
   an imaging unit including mounting means attachable to said ocular portion, imaging means facing said ocular window in a case of attachment to said ocular portion and having an imaging device, and a connector capable of being connected to said signal connector;
   signal processing means having a connector receiver capable of being connected to said signal connector, said signal processing means performing processing of an image signal supplied from said imaging means; and
   display means for displaying an image signal output from said signal processing means.

2. An endoscope system according to claim 1, wherein said light emergence means for issuing illumination light includes a lamp accommodated in said insertion portion on the side of said head thereof.

3. An endoscope system according to claim 1, further comprising a video tape recording means capable of being mounted on said ocular portion of said endoscope, said video tape recording means having:
   an imaging device;
   drive signal generation means for generating a signal for driving said imaging device;
   TV signal generation means for forming a TV signal from a signal output from said imaging device;
   modulation means for modulating a signal output from said imaging device;
   a rotary head to which a signal modulated by said modulation means is added; and
   a magnetic tape used for magnetic recording performed by said rotary head.

4. An endoscope system according to claim 1, said signal processing means has a freeze angle memory.

5. An endoscope system according to claim 4, said imaging unit has a freeze angle switch and adapted to stop update of writing in said freeze angle memory via said signal transmission line(s).

6. An endoscope system according to claim 1, wherein said light emergence means for issuing illumination light comprises a light guide having an emergence-end surface disposed at said head of said insertion portion and a light source for supplying illumination light to an incident-end surface of said light guide.

7. An endoscope system according to claim 6, wherein said light source includes a lamp which outputs white light.

8. An endoscope system according to claim 6, further comprising a housing means for accommodating said light source and said signal processing means.

9. An endoscope system according to claim 6, wherein said light source includes a lamp which outputs white light, a rotary disk color filter having a plurality of color transmissible filters disposed in the peripheral direction, and a motor for rotating said rotary color filters.

10. An endoscope system according to claim 9, further comprising means for moving said rotary color filters and said motor in directions in which said rotary color filters and said motor can be placed in or removed from the optical path of illumination light emitted from said lamp.

11. An endoscope system according to claim 1, further comprising an electronic endoscope having: an elongated insertion portion;
light emergence means for issuing illumination light, at least part of said light emergence means being disposed at a head of said insertion portion;
an objective optical system disposed in a head portion of insertion portion;
a solid-state imaging device inserted into said insertion portion and disposed on a focal plane of said objective optical system;
signal line(s) inserted into said insertion portion;
a signal cable extending from a rear portion of said insertion portion to the outside, a part of said signal line(s) being inserted into said signal cable; and
a signal connector attached to an end of said signal cable and connected to said signal line(s).

12. An endoscope system according to claim 11, wherein said light emergence means for issuing illumination light in said electronic endoscope includes a light guide.

13. An endoscope system according to claim 11, wherein said light emergence means for issuing illumination light in said electronic endoscope includes a lamp accommodated in said head portion of said insertion portion.

14. An endoscope system according to claim 11, said signal connector of said electronic endoscope has means for generating a drive signal for driving said solid-state imaging device.

15. An endoscope system according to claim 11, wherein said signal processing means is used in common for said electronic endoscope and said imaging unit.

16. An endoscope system according to claim 11, wherein said electronic endoscope can be used in place of said endoscope on which said imaging unit is mounted.

17. An endoscope system according to claim 11, further comprising a semiconductor memory for storing an image signal output from said solid-state imaging device.

18. An endoscope system according to claim 17, further comprising means for reading image signal data written in said semiconductor memory.

19. An endoscope system according to claim 1, further comprising an electronic camera capable of being connected to said ocular portion of said endoscope, said electronic camera having:
an imaging device;
drive signal generation means for generating a drive signal for driving said imaging device;
TV signal generation means for forming a TV signal from a signal output from said imaging device; and
recording means for recording a signal output from said imaging device.

20. An endoscope system according to claim 19, wherein said electronic camera has a photometry means for detecting exposure of said imaging device.

21. An endoscope system according to claim 20, wherein said electronic camera has a TV signal output terminal and a signal output terminal of said photometry means, said output terminals being disposed on a mount portion of said electronic camera for mounting on said ocular portion.

22. An endoscope system according to claim 21, wherein said two signal output terminals are positioned in such a manner that they face contacts provided in said signal connector receiver.

23. An endoscope system according to any one of claims 1 to 11, wherein said imaging unit has no external cable.

24. An endoscope system according to either one of claims 1 or 11, further comprising a semiconductor memory for storing an image signal output from said imaging unit.

25. An endoscope system according to claim 24, further comprising means for reading image signal data written in said semiconductor memory.

26. An external imaging unit attachment type of endoscope comprising:
an endoscope including an elongated insertion portion, light emergence means for issuing illumination light from a head of said insertion portion, an objective optical system disposed in a head portion of said insertion portion, an image guide inserted into said insertion portion and adapted to transmit an optical image imaged by said objective optical system, an ocular portion having an ocular window facing an emergence end of said image guide, a signal cable extending from a rear end of said insertion portion or from said ocular portion to the outside and provided with signal transmission line(s) inserted into said signal cable, a signal connector receiver provided on said ocular portion and connected to one end of said signal transmission line(s), and a signal connector attached to a head of said signal cable and connected to the other end of said signal transmission line(s); and
an imaging unit including mounting means attachable to said ocular portion, imaging means facing said ocular window and having an imaging device, and a connector capable of being connected to said signal connector.

27. An endoscope according to claim 26, further comprising a semiconductor memory for storing an image signal output from said imaging means.

28. An endoscope according to claim 26, wherein said signal connector of said imaging unit is disposed in the vicinity of said mounting means.

29. An endoscope according to claim 26, wherein said imaging unit has a signal transmission line for transmitting, without any modulation, a signal output from said imaging device to said signal connector of said imaging unit.

30. An endoscope according to claim 26, wherein said light emergence means for issuing illumination light includes a light guide having an emergence-end surface disposed at said head of said insertion portion.

31. An endoscope according to claim 26, wherein said light emergence means for issuing illumination light includes a lamp disposed at said head of said insertion portion.

32. An endoscope according to claim 26, wherein said signal transmission line(s) include(s) an optical cable.

33. An endoscope according to claim 26, wherein said imaging means has means for generating a drive signal in conformity with the number of picture elements of said imaging device.

34. An endoscope according to either one of claims 26 or 33, wherein said imaging unit has voice input means.

35. A endoscope according to either one of claims 26 or 33, wherein said imaging unit further includes:
 TV signal generation means for forming a TV signal from a signal output from a signal output from said imaging device;
 modulation means for modulating a signal output from said imaging device;
 recording means for recording a modulated signal supplied from said modulation means; and
 signal transmission means for transmitting said TV signal to said signal connector.

36. An endoscope according to claim 35, wherein said recording means has a recording medium in the form of a disk.

37. An endoscope according to claim 35, wherein said recording means has a recording medium in the form of a tape.

38. An endoscope according to claim 35, wherein said imaging unit further includes photometry means for measuring exposure of said imaging device.

39. An endoscope according to claim 38, further comprising signal transmission means for transmitting a signal output from said photometry means to said signal connector.

40. An endoscope according to either one of claims 22 or 33, wherein said imaging unit further includes:
 modulation means for modulating a signal output from said imaging device; and
 signal transmission means for transmitting a signal output from said modulation means to said signal connector.

41. An endoscope according to claim 40, wherein said imaging unit further includes voice input means.

42. An endoscope according to claim 41, further comprising voice signal modulating means for modulating a voice signal output from said voice input means.

43. An endoscope according to claim 42, further comprising mixing means for superposing a modulated signal from said voice signal modulating means on a signal output from said modulation means.

44. An endoscope according to claim 40, wherein said imaging unit further includes control signal generation means.

45. An endoscope according to claim 44, further comprising a control signal modulating means for modulating a control signal supplied from said control signal generation means.

46. An endoscope according to claim 45, further comprising mixing means for superposing said control signal on a signal output from said modulation means.

47. An endoscope with signal transmission line(s) comprising:
 an elongated insertion portion;
 light emergence means for issuing illumination light from a head of said insertion portion;
 an objective optical system disposed in a head portion of said insertion portion;
 an image guide for transmitting an optical image imaged by said objective optical system;
 an ocular portion having an ocular window facing an emergence end of said image guide;
 a signal cable extending from a rear end of said insertion portion or from said ocular portion to the outside and provided with signal transmission line(s) at least for transmission of video signal inserted into said signal cable;
 a signal connector receiver provided on said ocular portion and connected to one end of said signal transmission line(s); and
 a signal connector attached to a head of said signal cable and connected to the other end of said signal transmission line(s).

48. An endoscope according to claim 47, wherein said light emergence means for issuing illumination light includes a lamp accommodated in said insertion portion on the side of said head thereof.

49. An endoscope according to claim 47, wherein said light emergence means for issuing illumination light includes a light guide having an emergence-end surface disposed at said head of said insertion portion.

50. An endoscope according to claim 49, further comprising a light guide cable extending from a position between the rear end of said insertion portion and the front end of said ocular portion to the outside.

51. An endoscope according to claim 50, wherein said signal cable is integral with said light guide cable.

52. An endoscope according to claim 50, wherein said signal cable and said light guide cable are two cables separated from each other.

53. An endoscope according to claim 50, wherein said signal cable and said light guide cable are constituted by a cable which diverges at its intermediate portion.

54. An endoscope according to claim 50, wherein said signal transmission line(s) include(s) an optical cable.

* * * * *